US012048605B2

(12) United States Patent
Farkash et al.

(10) Patent No.: US 12,048,605 B2
(45) Date of Patent: Jul. 30, 2024

(54) TRACKING ORTHODONTIC TREATMENT USING TEETH IMAGES

(71) Applicant: Align Technology, Inc., San Jose, CA (US)

(72) Inventors: Shai Farkash, Hod HaSharon (IL); Avi Kopelman, Palo Alto, CA (US); Maayan Moshe, Ramat HaSharon (IL); Eliahou Franklin Nizard, Jerusalem (IL); Jonathan Coslovsky, Rehovot (IL)

(73) Assignee: Align Technology, Inc., San Jose, CA (US)

( * ) Notice: Subject to any disclaimer, the term of this patent is extended or adjusted under 35 U.S.C. 154(b) by 469 days.

(21) Appl. No.: 17/174,038

(22) Filed: Feb. 11, 2021

(65) Prior Publication Data

US 2021/0244502 A1    Aug. 12, 2021

Related U.S. Application Data

(60) Provisional application No. 62/975,148, filed on Feb. 11, 2020.

(51) Int. Cl.
| | |
|---|---|
| *A61C 7/00* | (2006.01) |
| *G06N 20/00* | (2019.01) |
| *G06T 11/00* | (2006.01) |
| *G16H 30/40* | (2018.01) |
| *G16H 50/70* | (2018.01) |

(52) U.S. Cl.
CPC ............. *A61C 7/002* (2013.01); *G06N 20/00* (2019.01); *G06T 11/005* (2013.01); *G16H 30/40* (2018.01); *G16H 50/70* (2018.01)

(58) Field of Classification Search
CPC ...... A61C 7/002; A61C 9/0046; G06N 20/00; G06T 11/005; G16H 30/40; G16H 50/70; G16H 20/30; G16H 50/50; A61B 5/0077; A61B 5/0088; A61B 5/1111; A61B 5/1114; A61B 5/7267
See application file for complete search history.

(56) References Cited

U.S. PATENT DOCUMENTS

| | | | |
|---|---|---|---|
| 5,975,893 A | 11/1999 | Chishti et al. | |
| 6,227,850 B1 | 5/2001 | Chishti et al. | |
| 6,227,851 B1 | 5/2001 | Chishti et al. | |
| 6,299,440 B1 | 10/2001 | Phan et al. | |
| 6,318,994 B1 | 11/2001 | Chishti et al. | |

(Continued)

FOREIGN PATENT DOCUMENTS

CN    101969877 A    2/2011

*Primary Examiner* — Santiago Garcia
(74) *Attorney, Agent, or Firm* — Shay Glenn LLP

(57) ABSTRACT

Systems and methods for monitoring a subject's teeth during orthodontic treatment. An input 2D image of the subject's current teeth including a wide angle occlusal view of the subject's upper and/or lower jaw at a current treatment stage can be received. Virtual camera parameters corresponding to the input 2D image can be determined. A rendered 2D image of the subject's teeth can be generated from a 3D model of the subject's upper and/or lower jaw at a planned treatment stage with the virtual camera parameters. Differences between the subject's teeth from the input 2D image and the rendered 2D image using tooth centers can be determined. An indicator indicating the differences can be output.

20 Claims, 14 Drawing Sheets

(56) References Cited

U.S. PATENT DOCUMENTS

| | | |
|---|---|---|
| 6,371,761 B1 | 4/2002 | Cheang et al. |
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,554,611 B2 | 4/2003 | Chishti et al. |
| 6,582,229 B1 | 6/2003 | Miller et al. |
| 6,602,070 B2 | 8/2003 | Miller et al. |
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,134,874 B2 | 11/2006 | Chishti et al. |
| 7,156,661 B2 | 1/2007 | Choi et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,562,338 B2 | 10/2013 | Kitching et al. |
| 8,591,225 B2 | 11/2013 | Wu et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,492,245 B2 | 11/2016 | Sherwood et al. |
| 9,585,549 B1* | 3/2017 | Elazar ................ G06T 5/009 |
| 9,642,678 B2 | 5/2017 | Kuo |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2* | 9/2020 | Pokotilov ................ A61C 7/08 |
| 10,779,718 B2 | 9/2020 | Meyer et al. |
| 10,792,127 B2 | 10/2020 | Kopelman et al. |
| 10,810,738 B1* | 10/2020 | Chen ...................... G06T 19/00 |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 11,020,205 B2 | 6/2021 | Li et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,071,608 B2 | 7/2021 | Derakhshan et al. |
| 11,096,763 B2 | 8/2021 | Akopov et al. |
| 11,116,605 B2 | 9/2021 | Nyukhtikov et al. |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2008/0306724 A1 | 12/2008 | Kitching et al. |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2013/0204599 A1 | 8/2013 | Matov et al. |
| 2013/0286174 A1* | 10/2013 | Urakabe .......... A61B 1/000095 348/66 |
| 2013/0308846 A1* | 11/2013 | Chen ..................... A61B 6/463 382/131 |
| 2015/0265374 A1* | 9/2015 | Masoud ............... G06V 40/171 382/128 |
| 2016/0012182 A1* | 1/2016 | Golay ................... G16H 40/20 705/3 |
| 2016/0135925 A1 | 5/2016 | Mason et al. |
| 2016/0228212 A1* | 8/2016 | Salah .................. A61B 5/0013 |
| 2016/0242870 A1 | 8/2016 | Matov et al. |
| 2016/0310235 A1 | 10/2016 | Derakhshan et al. |
| 2017/0273760 A1 | 9/2017 | Morton et al. |
| 2018/0263733 A1* | 9/2018 | Pokotilov ................ A61C 7/08 |
| 2018/0280118 A1 | 10/2018 | Cramer |
| 2018/0284727 A1* | 10/2018 | Cramer ................ B33Y 50/02 |
| 2018/0303581 A1* | 10/2018 | Martz .................... A61C 7/002 |
| 2019/0015177 A1* | 1/2019 | Elazar .................... A61C 7/002 |
| 2019/0029784 A1 | 1/2019 | Moalem et al. |
| 2019/0053876 A1 | 2/2019 | Sterental et al. |
| 2019/0125493 A1* | 5/2019 | Salah .................... G16H 50/70 |
| 2019/0133717 A1* | 5/2019 | Salah .................... G16H 50/50 |
| 2019/0192259 A1 | 6/2019 | Kopelman et al. |
| 2019/0328487 A1 | 10/2019 | Levin et al. |
| 2019/0328488 A1 | 10/2019 | Levin et al. |
| 2019/0333622 A1 | 10/2019 | Levin et al. |
| 2019/0343601 A1 | 11/2019 | Roschin et al. |
| 2020/0000552 A1 | 1/2020 | Mednikov et al. |
| 2020/0000554 A1 | 1/2020 | Makarenkova et al. |
| 2020/0000555 A1 | 1/2020 | Yuryev et al. |
| 2020/0085546 A1 | 3/2020 | Li et al. |
| 2020/0105028 A1 | 4/2020 | Gao et al. |
| 2020/0107915 A1 | 4/2020 | Roschin et al. |
| 2020/0155274 A1 | 5/2020 | Pimenov et al. |
| 2020/0214800 A1 | 7/2020 | Matov et al. |
| 2020/0297458 A1 | 9/2020 | Roschin et al. |
| 2020/0306011 A1 | 10/2020 | Chekhonin et al. |

(56) References Cited

U.S. PATENT DOCUMENTS

| | | |
|---|---|---|
| 2020/0306012 A1 | 10/2020 | Roschin et al. |
| 2020/0315744 A1 | 10/2020 | Cramer |
| 2020/0360109 A1 | 11/2020 | Gao et al. |
| 2021/0073998 A1 | 3/2021 | Brown et al. |
| 2021/0134436 A1 | 5/2021 | Meyer et al. |
| 2021/0174477 A1 | 6/2021 | Shi et al. |
| 2021/0366136 A1* | 11/2021 | Lancelle ................ A61C 13/34 |
| 2023/0000600 A1* | 1/2023 | Wong .................. A61C 9/0053 |

* cited by examiner

FIG. 1D

TOOTH COMPARISON ENGINE(S)
164a

TOOTH MOVEMENT ENGINE 184

TOOTH MOVEMENT DATASTORE 186

TRACKING ORTHODONTIC TREATMENT USING TEETH IMAGES

CLAIM OF PRIORITY

This patent application claims priority to U.S. Provisional Patent Application No. 62/975,148, titled "AT HOME PROGRESS TRACKING USING WIDE ANGLE CAMERA," and filed on Feb. 11, 2020, herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Orthodontic procedures typically involve repositioning an individual's teeth to a desired arrangement in order to correct malocclusions and/or improve aesthetics. To achieve these objectives, orthodontic appliances such as braces, shell aligners, and the like can be applied to the individual's teeth by an orthodontic practitioner and/or by the individuals themselves. The appliance can be configured to exert force on one or more teeth in order to effect desired tooth movements according to a treatment plan.

Orthodontic aligners may include devices that are removable and/or replaceable over the teeth. Orthodontic aligners may be provided as part of an orthodontic treatment plan. In some orthodontic treatment plans involving removable and/or replaceable aligners, an individual may be provided plurality of orthodontic aligners over the course of treatment to make incremental position adjustments to the individual's teeth. An orthodontic aligner may have a polymeric trough with an inner cavity shaped to receive and resiliently reposition teeth from one tooth arrangement to a successive tooth arrangement. Orthodontic aligners may include "active" regions that impose repositioning forces on teeth and "passive" regions that retain teeth in their current state.

Treatment planning typically uses a 3D dental model created from a scan or dental mold of an individual's teeth. The 3D dental model can comprise, for example, raw tooth point clouds, tooth meshes, or reduced parameter representations of 3D teeth.

During the course of a treatment plan involving a series of dental aligners that is configured to move a subject's teeth to a desired configuration, it is sometimes beneficial to check the subject's teeth to confirm that they are moving in expected and/or desired manner, according to the treatment plan.

SUMMARY OF THE DISCLOSURE

Described herein are methods and apparatuses that may provide low-cost and simplified ways to confirm a treatment plan at one or more stages of the treatment plan. In particular, these methods and apparatuses may provide techniques (e.g., methods) and apparatuses for the patient or caregiver to assist in tracking or monitoring of a treatment plan without requiring the use of expensive or complex devices. For example, described herein are methods and apparatuses that may be used with a patient or caregiver's personal phone. In some examples, an attachment or other device may be coupled to the patient or caregiver phone; these accessory devices may be adapted for use with software, hardware or firmware for assisting in taking images (or guiding a user subject to take images) of sufficiently high quality so that the images may accurately track the patient's teeth in a treatment plan.

Of particular interest herein are methods and apparatuses for assisting a subject, e.g., a patient or caregiver (e.g., parent, guardian, etc.), collectively referred to herein as a "user subject", in collecting one or more images of sufficient size and with sufficient information about distance from the teeth, etc., so as to capture enough of the dentition so that it may be readily analyzed by one or more automated agents (including machine learning agents, other software, etc.) and/or manual agents (e.g., technician, dental professional, etc.). Although in the user subject may be distinct from the user professional, the user subject may be a professional user. For example, a professional user may use the methods and/or apparatuses described herein on a patient, and therefore act as both the user subject and the professional user.

In some examples, the user subject may be directed to take multiple images of the patient's teeth and/or oral cavity using a phone camera. In some examples, the phone camera may be calibrated or set so that the resulting images may be combined to form one or more images of the entire upper, lower or both upper and lower jaws, and may process the resulting image(s) to identify, register, and/or track movement of one or more teeth within the subject's upper and/or lower jaw. In some examples, one or more adapters (e.g., attachments) include optical components, such as one or more lenses or the like, may be included. In some examples, the lens(es) may be wide angle (e.g., "fisheye") lenses.

For example, any of these methods and apparatuses (e.g., systems, devices, etc.) may use a subject-operated wide angle (e.g., fish-eye) imaging system to capture one or more (or in some cases, just a single image) of the subject's dentition and determine (and/or indicate to the subject) if the subject needs to see the dental plan provider to modify or adjust the treatment plan.

Described herein are methods and systems for monitoring a dental subject's progress during a course of treatment. At any particular point in time during the course of treatment, a three-dimensional model of the expected positions of the subject's teeth at that point in time can be projected, in time, from a three-dimensional (3D) model of the subject's teeth prepared prior to beginning the treatment. During the course of treatment, a camera having a wide angle (e.g., fisheye) lens may be used to take a two-dimensional (2D) image of the subject's teeth, typically the occlusal surface of one or both jaws (including as a single image). The 2D image may include an occlusal view of both arches of the subject's dentition or a single (e.g., the upper or lower) arch. The 2D image represents the actual positions of the subject's teeth at that particular point in the orthodontic treatment. This 2D image may be referred to herein as the "original image" or an input 2D image.

The input 2D image can be provided to a monitoring system that is configured to determine camera parameters (also referred to herein as virtual camera parameters) of the camera having the wide angle lens that was used to take the input 2D image. The virtual camera parameters include both intrinsic parameters for the camera (e.g., the optical parameters for the camera) and extrinsic parameters for the camera (e.g., the location of the camera in space when taking the image). The extrinsic parameters may be determined with respect to the teeth. The monitoring system can use these camera parameters to generate a rendered 2D image from the 3D model of the subject's teeth, where the 3D model may correspond to the subject's teeth at a particular time or stage of the treatment plan. Typically this particular time or stage of the treatment plan may correspond to the current, actual time or stage that the subject is experiencing when the input 2D image was taken, allowing comparison of the expected (from the 3D model) to actual (from the input 2D image) positions of the teeth during the treatment plan. In some examples, however, it may be desirable to compare the current position of the subject's teeth (e.g., from the input 2D image) with one or more other stages of the treatment plan, including the initial position of the teeth; in this case, the 3D model used to generate the rendered 2D image may instead correspond to another stage of the treatment plan or the initial position of the subject's teeth prior to starting the treatment plan.

The monitoring system can compare the input 2D image to the rendered 2D image to determine how closely the actual or current position of the subject's teeth tracks with the expected or desired positions according to the orthodontic treatment plan. The methods and systems described herein may do this comparison in a fast and effective manner by determining the positions of the teeth centers in both the input 2D image and the rendered 2D image, and by comparing silhouettes of corresponding teeth in input 2D image to the rendered 2D image. These steps may be performed after segmentation of the teeth in the input 2D image and the rendered 2D image. In some examples, the 3D tooth model may include segmentation information for each tooth that may be used to segment the rendered 2D image. The rendered 2D image may be segmented separately from the input 2D image. In some examples, the segmentation of the rendered 2D image (which may be expected to be approximately similar to the rendered 2D image), may be used to help segment the input 2D image.

Any appropriate method may be used to determine the 2D tooth centers from the input 2D image. For example, the 2D centers of the teeth may be identified manually or automatically, or semi-automatically. In some examples, machine learning (e.g., forming a trained network) may be used to find the 2D centers of the teeth from the occlusal view provided by the wide angle (e.g., fisheye) image. Similarly, any appropriate technique may be used to determine the tooth centers of the rendered 2D image. In some examples, the tooth centers of the rendered 2D image may be identified from the 3D model of the teeth prior to generating the rendered 2D image using the virtual camera parameters. Alternatively, in some examples, the tooth centers for the rendered 2D image may be determined directly from the rendered 2D image. For example, in some examples, the rendered 2D image may be analyzed using the same technique used to determine the tooth centers from the input 2D image (e.g., using a trained neural network) may be used.

In some examples, the tooth centers from the input 2D image may be compared to the tooth centers from the rendered 2D image to provide an estimate of the differences and/or agreement between the tooth centers of the rendered 2D images and the input 2D image. Comparison of the tooth centers may provide an estimate of translational movement of the teeth (for example, x, y translation of the teeth) between the treatment plan and the subject's actual teeth. Alternatively or additionally, the comparison of the contours (e.g., silhouettes) of the teeth in the rendered 2D images to the input 2D images may provide an estimate of rotational movement of the teeth (e.g., as the rotation required to align the teeth of the input 2D image to the rendered 2D image). In some examples, just the silhouettes of the segmented teeth may be compared to determine both translational and rotational movement, however, in some examples, it may be beneficial to use the tooth centers to identify movement quickly and accurately to provide an estimate of tooth movement. As described herein, estimates of tooth movement using tooth centers may be done quickly and may require fewer computations. In some examples, more accurate tooth movement estimates, including estimates of rotation, may not be necessary.

Any of the methods and systems described herein may use the comparison between the input 2D image (based on, e.g., a wide angle image of the occlusal surface of the teeth taken by the subject) and the rendered 2D image to generate one or more scores (difference scores) related to the difference in tooth position(s) between the input 2D image and the rendered 2D image. This score or scores may indicate the severity of the differences between the input 2D image and the rendered 2D image. For example, a difference score may be a measure of the total deviation of all of the segmented teeth in translation and/or rotation. In some examples, separate scores may be used to reflect the difference in different teeth. In some examples, separate scores may be used to reflect the differences between translation and rotation. The score(s) may be weighted and/or scaled. For example, the score may value translation more than rotation, may value rotation more than translation, may value some teeth more than other teeth (such as molars more than pre-molars, more than incisors, etc.), or the like. The score may be normalized or averaged.

In some examples, the one or more difference score may be provided to the subject and/or to the dental professional ("dental professional user" or simply "professional user". For example, the method or apparatus may include alerting the dental professional user (e.g., the physician, dentist, orthodontist, or other dental professional) when the difference score(s) is/are above threshold value(s). In some examples, the threshold value(s) may be pre-set and/or may be set by the professional user. For example, in some examples, the subject may be using an application software (e.g., "app") for their hand-held device, such as a smartphone, that includes a wide angle (e.g., fisheye) lens for the camera. The application software may guide the subject in taking the wide angle image, and may process the image (locally using the one or more processors in the hand-held device, or remotely by passing the image onto a remote server). The processed input 2D image may then be analyzed a described herein to determine the difference and, if the difference score exceeds a notification threshold, may instruct the user subject to make an appointment with their dental care provide (e.g., the professional user) to adjust the treatment plan. In some examples, the difference score may trigger notifications to the subject to wear the aligner more frequency or otherwise be more diligent in complying with the treatment plan.

The comparison between the subject's dentition, e.g., the subject's tooth positions at the current treatment stage, and the expected or predicted tooth positions for the subject's teeth at a particular treatment stage from the 3D model of the subject's teeth may be output as a difference indicator. The difference indicator may be a difference map, a difference score and/or a set of difference values. The difference indicator may be output by the method or system.

For example, in any of the methods and systems described herein, the difference(s) between the input 2D image and the rendered 2D image (e.g., the difference indicator) may provide difference information instead, or in addition to, one or more difference scores. For example, the method or system may generate a difference map, visually showing which teeth are diverging from the treatment plan and by how much. In some examples, the difference map may be formed as a composite between the input 2D image and the rendered 2D image, highlighting the differences (by one or more of symbols, text, colors, etc.).

In any of these methods and systems the difference(s) between the input 2D image and the rendered 2D image (e.g., the difference indicator) may be provided as a set of difference values, such as a listing, spreadsheet, dataset, etc. providing alphanumeric data summarizing or listing the differences between the input 2D image and the rendered 2D image.

The difference indicator (e.g., difference map, difference score and/or difference values) may be stored, displayed and/or transmitted (for storage and/or display), including transferring to the professional user (e.g., the subject's dental provider) or a third party. In some examples, the images displayed (including but not limited to the input 2D image and the rendered 2D images, may be adjusted to reduce or remove the distortion of the images due to the wide angle camera assembly.

For example, described herein are methods, including methods of determining a subject's progress for a treatment plan (e.g., determining deviations from a treatment plan). These methods may also be methods of alerting a subject's dental practitioner (a professional user, such as a dentist, orthodontist, etc.) of deviations from a dental treatment plan, and/or method of correcting or updating a dental treatment plan. For example, a method may include: receiving an input 2D image from a wide angle (e.g., fisheye) camera comprising an occlusal view of a first arch and/or a second arch of the patient's dentition; identifying tooth features for teeth in the first arch and/or second arch in the input 2D image; determining virtual camera parameters from the input 2D image; receiving a 3D model of the patient's dentition (e.g., at a target treatment plan stage or time); generating a rendered 2D image from the 3D model using the virtual camera parameters; identifying tooth features for teeth in the first arch and/or second arch in the rendered 2D image; and comparing the tooth features of the rendered 2D image to the tooth features of the input 2D image. Any of these methods may also include outputting a difference indicator indicating the difference between the subject's current teeth and the planned treatment stage based on the difference between the teeth from the input 2D image and the rendered 2D image.

For example, identifying the tooth features may include applying a trained machine learning model to the 2D fisheye photo. In some examples, identifying the tooth features comprises manually identifying the tooth features. The tooth features may comprise tooth centers. The tooth features may comprise tooth silhouettes. In some examples, the tooth features provide a position and orientation of the patient's teeth.

The input 2D image may represents an actual positions of the patient's teeth at that particular point in an orthodontic treatment (e.g., at a particular stage of a treatment plan), while the rendered 2D image may represent an expected or desired positions of the patient's teeth (at the corresponding stage of the treatment plan), based on a synthesized 3D model of the patient's teeth predicting tooth position at the corresponding stage.

In some examples, the comparison indicates how closely the patient's teeth are tracking with the orthodontic treatment plan.

As mentioned, any of these methods may include updating the orthodontic treatment plan based on the comparison.

For example, updating may include calculating new teeth movements that are required to move the patient's teeth from the current position to the desired position. In some examples, updating may include updating the orthodontic treatment plan with these new teeth movements.

As described herein, a method, such as a method of determining a subject's progress for a treatment plan and/or deviations from a treatment plan, methods of alerting a subject's dental practitioner of deviations from a dental treatment plan, and/or method of correcting or updating a dental treatment plan, may include: receiving an input 2D image of a subject's teeth comprising a wide angle occlusal view of the subject's upper and/or lower jaw at a current treatment stage; determining virtual camera parameters corresponding to the input 2D image; receiving a 3D model of the subject's upper and/or lower jaw at a planned treatment stage; generating a rendered 2D image of the subject's teeth from the 3D model with the virtual camera parameters; determining differences between the teeth from the input 2D image and the rendered 2D image using tooth centers; and outputting a difference indicator indicating the difference between the subject's current teeth and the planned treatment stage based on the difference between the teeth from the input 2D image and the rendered 2D image.

In some examples, a method as described herein may include: receiving an input 2D image of a subject's teeth comprising a wide angle occlusal view of the subject's upper and/or lower jaw at a current treatment stage; determining virtual camera parameters corresponding to the input 2D image; receiving a 3D model of the subject's upper and/or lower jaw at a planned treatment stage; generating a rendered 2D image of the subject's teeth from the 3D model with the virtual camera parameters; determining translation differences between the teeth from the input 2D image and the rendered 2D image using tooth centers; determining rotational differences between the teeth from the input 2D image and the rendered 2D image using silhouettes of the teeth; and outputting a difference indicator indicating the difference between the subject's current teeth and the planned treatment stage.

Thus, any of these methods may include determining either or both translational differences and/or rotational differences of the teeth. For example, any of these methods may include determining rotational differences between the teeth from the input 2D image and the rendered 2D image using silhouettes of the teeth, wherein the difference indicator is further based on the rotational differences. Rotational differences and/or translational differences between the teeth from the 2D image and the rendered 2D image may be determined in whole or in part by applying a trained machine learning model to the input 2D image and the rendered 2D image. Any of these methods may include receiving the input 2D image comprises guiding a subject to take the wide angle occlusal image. The difference indicator may be one or more of: a difference map, a difference score and/or a set of difference values.

In general, the input 2D image may be used to determine the virtual camera parameters, and in particular the extrinsic camera parameters. In some examples, the input 2D image may be used to determine the intrinsic camera parameters. Alternately, in some examples, some or all of the intrinsic camera parameters may be preset or predetermined (e.g., factory set, input by the camera and/or lens providers, etc.). In some examples, the virtual camera parameters comprises may be iteratively determined from the input 2D image.

The methods and apparatuses described herein may operate off of a single input 2D image, e.g., a single image taken by a wide angle (e.g., fisheye) lens. In some examples, receiving the input 2D image of a subject's teeth may comprise receiving a fisheye view of both the subject's upper and lower jaw. The wide angle image may be a fisheye image. For example, the wide angle image may have a field of vision covering up to 160 degrees or more (e.g., up to 170 degrees or more, up to 180 degrees or more, up to 190 degrees or more, up to 200 degrees or more, up to 210 degrees or more, up to 220 degrees or more, up to 230 degrees or more, up to 240 degrees or more, up to 250 degrees or more, up to 260 degrees or more, up to 270 degrees or more, etc.). The wide angle image may include an occlusal (or occlusal perspective) view of all of the subjects teeth for both the upper and lower jaws. This may beneficially allow a single image to be processed as described herein. In some examples, the combination of the wide angle image and the use tooth centers to determined translational differences and tooth silhouettes to determine rotational permits extremely rapid and accurate determinations of differences in tooth configurations between actual tooth position and predicted (e.g., projected or modeled) tooth positions, requiring less processing power and operating more robustly on subject-generated input 2D images.

Any of the methods described herein may include determining a difference score. The difference score may be based on the difference indicator. Any of these methods may also include alerting the subject and/or the subject's dental care provider if the difference score exceeds a threshold. The subject's dental care provider may set or approve the threshold.

In some examples, the methods described herein may further include updating the orthodontic treatment plan based on the difference indicator. Alternatively or additionally, the methods described herein may include calculating new teeth movements that are required to move the subject's teeth from a current position to a desired position using the difference indicator, and/or updating the orthodontic treatment plan with these new teeth movements.

Also described herein are systems configured to perform any of the methods described herein. For example, a system may include a non-transitory computing device readable medium having instructions stored thereon for tracking a patient's teeth during an orthodontic treatment plan, wherein the instructions are executable by a processor to cause a computing device to: receive an input 2D image from a wide angle (e.g., fisheye) camera having an occlusal view of a first arch and a second arch of the patient's dentition; identify tooth features for teeth in the first arch and second arch in the input 2D image; determine virtual parameters of the wide angle camera corresponding to the input 2D image; receive a 3D model of the patient's dentition; generate a rendered 2D image from the 3D model with the virtual parameters of the wide angle camera; identify tooth features for teeth in the first arch and second arch in the rendered 2D image; compare the tooth features of the rendered 2D image to the tooth features of the input 2D image.

Any of the methods and apparatuses described herein may include one or more calibration steps. For example, a user subject (patient, caregiver, etc.) may be provided with a printed calibration standard (e.g., a calibration standard pattern or target, such as a checkerboard pattern) and/or may be instructed to print out (using a home printer) the calibration standard. The calibration standard may be included with the packaging. In some examples the packaging for the camera or a camera attachment (e.g., adapter, etc.) holding all or some of the optics (such as the wide angle lens) may be configured as a calibration jig that may both position the camera (optionally with the adapter) in a predefined position relative to a calibration standard. The user subject may then take several images (and may instructed by control software, e.g., on the user subject's phone) to take images of the calibration standard which may then be used by the method or apparatus to calibrate the user subject's camera (including a camera phone). In some examples, the apparatus or method may apply calibration logic to analyze the image(s) of the calibration standard and determine distance to the camera, etc.

For example, any of the systems described herein may include: one or more processors; a camera; a wide angle lens; and a memory coupled to the one or more processors, the memory configured to store computer-program instructions, that, when executed by the one or more processors, perform a computer-implemented method comprising: receiving an input 2D image of a subject's teeth comprising a wide angle occlusal view of the subject's upper and/or lower jaw at a current treatment stage; determining virtual camera parameters corresponding to the input 2D image; receiving a 3D model of the subject's upper and/or lower jaw at a planned treatment stage; generating a rendered 2D image of the subject's teeth from the 3D model with the virtual camera parameters; determining differences between the teeth from the input 2D image and the rendered 2D image using tooth centers; and outputting a difference indicator indicating the difference between the subject's current teeth and the planned treatment stage based on the difference between the teeth from the input 2D image and the rendered 2D image. These systems may be further configured so that the computer-implemented method performs any of the steps described above.

In some examples, the system is configured to include or operate on/with a hand-held computing and/or communications device, such as a smartphone, tablet, etc. Any of the steps described above may be performed locally (e.g., in the hand-held computing device) or they may be divided between local and remote processors. Remote processing may be performed on a remote server (e.g., cloud-based server) or the like.

In any of the methods and apparatuses described herein, the camera may be registered to the patient's jaw and/or teeth, as described herein. After registering the camera to the entire jaw the methods or apparatuses can register each tooth separately, as described above, and by doing this may use this information to detect the movement of the individual tooth to the entire jaw. For example, registration may be detected by matching tooth silhouette projection to the silhouette of the tooth on the image. In some examples, registration may be detected by, e.g., matching tooth cusps and\or fisher projection(s) to the image tooth cusp and\or fisher. In some example, registration may be detected by training a network that takes as an input the tooth image and a depth map of the tooth from the same camera and it produces the teeth movement. Any combination of these may be used. In general, registration from the image(s) can be done from a plurality of images and/or form a short video taken.

For example, described herein are methods including: calibrating a user subject's camera of the user subject's phone; receiving a plurality of input 2D images of a subject's upper and/or lower jaw taken with the calibrated user subject's camera; determining virtual camera parameters corresponding to the plurality of input 2D images; registering the camera to the subject's upper and/or lower jaw; receiving a 3D model of the subject's upper and/or lower jaw at a planned treatment stage; determining translation and/or rotational differences between individual teeth from the plurality of 2D images and the 3D model by individually registering teeth of subject's upper and/or lower jaw; and outputting a difference indicator indicating the difference between the subject's current teeth and the planned treatment stage.

The plurality of input 2D images may be combined into a single image (e.g., a merged image). Calibrating the user subject's camera may include determining virtual camera parameters.

Any of these methods may include generating a rendered 2D image of the subject's teeth from the 3D model with virtual camera parameters from the user subject's camera. The rendered 2D images may be used for comparison with the plurality of 2D images (or a merged 2D image).

The methods described herein may determine translation and/or rotational differences between the teeth from the input 2D image and the 3D model by registering individual teeth of the subject's upper and/or lower jaw. For example, registering individual teeth may include matching tooth silhouette projection between the rendered and input 2D images. In some examples, registering individual teeth comprises matching tooth cusps and/or fisher projections between the rendered and input 2D images. In some examples, registering individual teeth comprises using a machine learning agent to determine differences between the teeth from the 2D image and the rendered 2D image.

Any of these methods may include instructing a user subject to print a calibration pattern and taking one or more images of the calibration pattern with the user subject's camera. These images may be used to calibrate the camera and/or image, including determining virtual camera parameters and/or determining the distance to the camera. The calibration pattern may comprise a checkerboard or grid pattern.

These methods may include calibrating the camera by generating the input 2D image of the subject's teeth.

Any of the methods described herein may be performed by a system configured to perform these methods. For example, a system may include: one or more processors; and a memory coupled to the one or more processors, the memory configured to store computer-program instructions, that, when executed by the one or more processors, perform a computer-implemented method comprising: calibrating a user subject's camera of the user subject's phone; receiving a plurality of input 2D images of a subject's upper and/or lower jaw taken with the calibrated user subject's camera; determining virtual camera parameters corresponding to the plurality of input 2D images; registering the camera to the subject's upper and/or lower jaw; receiving a 3D model of the subject's upper and/or lower jaw at a planned treatment stage; determining translation and/or rotational differences between individual teeth from the plurality of 2D images and the 3D model by individually registering teeth of subject's upper and/or lower jaw; and outputting a difference indicator indicating the difference between the subject's current teeth and the planned treatment stage.

Other examples of techniques and systems that may benefit from the methods and apparatuses described herein may be found, for example, in U.S. patent application Ser. No. 16/370,788, filed on Mar. 29, 2019 (titled "PHOTOGRAPH-BASED ASSESSMENT OF DENTAL TREATMENTS AND PROCEDURES"), which is a continuation of U.S. patent application Ser. No. 14/831,548, filed on Aug. 20, 2015 (titled "PHOTOGRAPH-BASED ASSESSMENT OF DENTAL TREATMENTS AND PROCEDURES"), which issued on Apr. 2, 2019 as U.S. Pat. No. 10,248,883. Each of these applications is herein incorporated by reference in its entirety.

In general, the methods and apparatuses described herein may be performed at very low cost and complexity for subject at-home monitoring, without requiring a dental practitioner or expensive scanning equipment.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1D is a diagram showing an example of a tooth comparison engine(s).

DETAILED DESCRIPTION

Figure 1A:
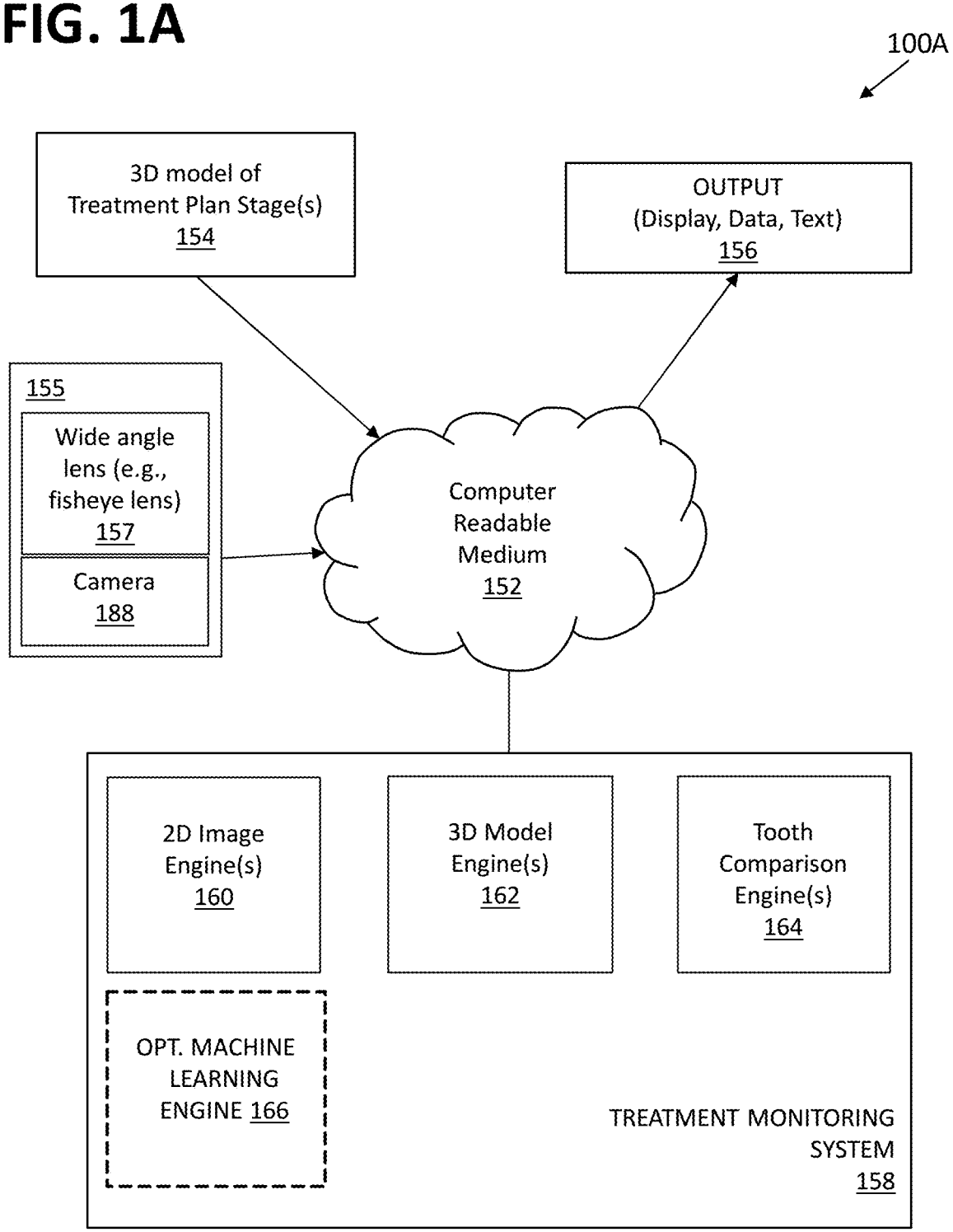
FIG. 1A is a diagram showing an example of a computing environment configured to monitor a subject's teeth during an orthodontic treatment plan.

Described herein are apparatuses (e.g., systems, computing device readable media, devices, etc.) and methods for monitoring, analyzing, correcting and/or tracking the progress of a subject's orthodontic treatment. The apparatuses and methods described herein can capture or receive as input a 2D image of the subject's teeth (input 2D image) taken by a wide angle (e.g., fisheye) and process this input 2D image to compare it with a model of the subject's dentition, such as a 3D digital model, to determine differences between the actual tooth configurations (from the input 2D image) and the predicted or desired tooth configurations (from the 3D model) at one or more stages of a treatment plan. The 3D model may represent the configuration of the subject's teeth at a particular stage of a treatment plan; in some examples, this stage may correspond to the stage that the subject's teeth are currently expected to be positioned. The 3D digital model may be generated at the start of a treatment plan, and may be used to design and manufacture a series of orthodontic appliances (e.g., aligners).

The methods described herein may use the input 2D image and/or predetermined values, to determine virtual camera parameters (e.g., intrinsic and extrinsic virtual camera parameters) for the camera taking the wide angle input 2D image. The virtual parameters can then be used to generate a rendered 2D image from a 3D dental model of the subject's teeth corresponding to the input 2D image, for comparison. The rendered 2D image may be compared against the input 2D image to generate a difference indicator such as a difference map, a difference score and/or a set of difference values. In some examples, the comparison can determine how closely the subject's teeth are tracking the desired orthodontic treatment plan.

The apparatuses and/or methods described herein may be useful in planning and fabrication of dental appliances, including elastic polymeric positioning appliances, is described in detail in U.S. Pat. No. 5,975,893, and in published PCT application WO 98/58596, which is herein incorporated by reference for all purposes. Systems of dental appliances employing technology described in U.S. Pat. No. 5,975,893 are commercially available from Align Technology, Inc., San Jose, Calif., under the tradename, Invisalign System.

Throughout the body of the Description of Embodiments, the use of the terms "orthodontic aligner", "aligner", or "dental aligner" is synonymous with the use of the terms "appliance" and "dental appliance" in terms of dental applications. For purposes of clarity, examples are hereinafter described within the context of the use and application of appliances, and more specifically "dental appliances."

As used herein, a "subject" (or alternatively and equivalently, an "individual") may be any subject (e.g., human, non-human, adult, child, etc.) and may be alternatively and may be a patient, a subject under treatment, or the like. A subject may be a medical patient. An individual or a subject may include a person who receives orthodontic treatment, including orthodontic treatment with a series of orthodontic aligners.

The apparatuses and/or methods (e.g., systems, devices, etc.) described below can be used with and/or integrated into an orthodontic treatment plan. The apparatuses and/or methods described herein may include segmenting an individual's teeth from a three-dimensional model, such as a 3D mesh model or a 3D point cloud. The methods and apparatuses described herein may segment the 2D images. Segmentation information may be used measure, compare, and process the 2D images. Segmenting the individual's teeth can be done automatically (e.g., using a computing device), manually or semi-automatically. For example, segmentation can be performed by a computing system automatically by evaluating data (such as three-dimensional scan, or a dental impression) of the individual's teeth or arch. Segmentation may be done using a trained network (e.g., as part of a machine-learning technique). One or more data structures (e.g., databases) may be used to assist in segmentation of the 2D images or 3D models. In some examples, the methods and apparatuses described herein may use the segmentation information from the input or received 3D model of the patient's teeth. Thus, the segmentation information of the teeth from the 3D model may be provided as an input and may be used to analyze the input 2D image, as well as any 2D images generated from the 3D model of the subject's teeth.

For example, a 3D model of the subject's teeth may be generated initially from an intraoral scanner scanning an individual's dental arch to generate a virtual three-dimensional model of that dental arch. During an intraoral scan procedure (also referred to as a scan session), a professional user (e.g., a dental practitioner) of an intraoral scanner may generate multiple different images (also referred to as scans or medical images) of a dental site, model of a dental site, or other object. The images may be discrete images (e.g., point-and-shoot images) or frames from a video (e.g., a continuous scan). The intraoral scanned images may be used to generate a 3D model which may be modified to form a 3D model of all or a portion of an orthodontic treatment plan ("treatment plan") having multiple stages for moving teeth to desired configurations, including a final (e.g., aligned) configuration. Although the methods and apparatuses described herein may incorporate (and may receive as input) intraoral scanning information, these apparatuses and methods described herein may be performed without requiring the use of an intraoral scanner. In particular, these methods and apparatuses may be operated by the subject in a home setting, allowing the subject to aid in monitoring, tracking and updating progress in a robust and inexpensive manner.

FIG. 1A is a diagram showing an example of a computing environment 100A configured to facilitate gathering and processing digital scans of a dental arch with teeth therein. The environment 100A includes a computer-readable medium 152 that is configured to receive a 3D model of the subject's teeth at one or more treatment stages 154, and to receive or include a wide angle camera assembly 155 including a camera 188 having or coupled with a wide angle (e.g., fisheye) lens or lenses 157, and treatment monitoring system 158. The system may be configured to output 156 images, text, data and/or alerts. The output 156 may be part of the treatment monitoring system, or it may be separate from the treatment monitoring system. The treatment monitoring system may include one or more modules (e.g., engines, data structures, etc.) for processing and comparing the 2D and 3D representation of the subject's teeth. One or more of the modules in the computing environment 100A may be coupled to one another or to modules not explicitly shown.

The computer-readable medium 152 and other computer readable media discussed herein represent a variety of potentially applicable technologies. For example, the computer-readable medium 152 can be used to form a network or part of a network. Where two components are co-located on a device, the computer-readable medium 152 can include a bus or other data conduit or plane. Where a first component is co-located on one device and a second component is located on a different device, the computer-readable medium 152 can include a wireless or wired back-end network or LAN. The computer-readable medium 152 can also encompass a relevant portion of a WAN or other network, if applicable.

The 3D model of the treatment plan stage(s) 154 may be received from a scanning system, a database, a computer system, or any other structure. The 3D model of one or more treatment plan stages may be a 3D model of an entire treatment plan or a subset of the treatment plan. The 3D model may include the treatment plan for the upper and lower dental arch. A "dental arch," as used herein, may include all or at least a portion of an individual's dentition formed by the individual's maxillary and/or mandibular teeth. A dental arch may include one or more maxillary or mandibular teeth of an individual, such as all teeth on the maxilla or mandible or an individual. The 3D model 154 may be stored in a memory, database and/or one or more processors and may be used to generate a rendered 2D image of the subject's teeth as well as to provide additional information about the subject's teeth, including tooth segmentation, etc. The 3D model may be associated with the particular subject. In some examples, the system may include a verification engine (not shown) that may confirm or verify that the 3D model of the treatment plan stage(s) corresponds to the specific subject for whom the input 2D image is taken. The 3D dental model(s) can comprise, for example, one or more 3D point cloud or 3D dental mesh. The treatment monitoring system 158 may be configured to receive 3D model data taken previously or by another system.

The wide angle camera assembly 155 may include a computer system or camera 188 configured to obtain wide angle 2D image(s) of a subject's dentition, e.g., operating with a wide angle lens 157. The wide angle lens may be part of the camera or may be added onto the camera. The wide angle camera assembly may be part of the treatment monitoring system 158 or it may be used with the treatment monitoring system 158. A wide angle 2D image, as described herein, may include ultra-wide 2D images produced with a wide angle (e.g., fisheye) camera or wide angle (e.g., fisheye) lens, in which the subject may have a convex non-rectilinear appearance. Wide angle 2D images of a subject's dentition may include, for example, an occlusal view (or perspective occlusal view) of both dental arches of a subject's teeth in a single 2D image. The wide angle camera assembly 155 may be, for example, a standalone camera or lens, or alternatively, a fisheye lens attachment for a smartphone, tablet or computer. The wide angle camera can be used by the subject during the course of an orthodontic treatment to take wide angle input 2D images of the subject's teeth (e.g., upper and/or lower arch).

The output 156 may include a computer system configured to display at least a portion of a dentition of an individual, and/or the difference(s) between the input 2D image (e.g., at a current treatment stage) and the modeled treatment plan stage(s) corresponding to the current treatment stage. The output 156 may include a display system, a memory, one or more processors, etc. The output may be part of a display device to display the individual's dentition. The output 156 may be implemented as part of a computer system, a dedicated intraoral scanner, etc. In some implementations, the output 156 facilitates display of an individual's dentition using scans that are taken at an earlier date and/or at a remote location. The output 156 may facilitate display of scans taken contemporaneously and/or locally to it. The output 156 may be configured to display the intended or actual results of an orthodontic treatment plan applied to a dental arch scanned by the scanning system 154. The results may include 3D virtual representations of the dental arch, 2D images or renditions of the dental arch, etc. In some examples, the output may be transmitted to the subject's dental care provider (e.g., orthodontist, dentist, dental practitioner, etc.) as one or more images, as text (e.g., a text file enumerating differences), as a score (e.g., a numeric or alphanumeric score), as a 3D model or modified 3D model, etc.

The treatment monitoring system 158 may include a computer system, including memory and one or more processors, configured as described herein to monitor a subject's dentition and track movement of the subject's teeth to an orthodontic treatment plan. For example, the treatment monitoring system may include a number of modules or engines for determining the differences between a patient's actual tooth configuration and the planned tooth configuration at one or more treatment stages. These modules or engines may correspond to one or more processors. The 2D image engine(s) 160 may implement automated agents to receive an input 2D image of the subject's teeth from a wide angle camera. The input 2D image can comprise, for example, an ultra-wide angle image that includes an occlusal view (or occlusal perspective view) of both arches of the subject's dentition. The input 2D image can represent the actual positions of the subject's teeth at that particular time or stage in the orthodontic treatment. The 2D image engine(s) 160 may be further configured to process the input 2D image to extract and identify tooth features of the subject's teeth. The tooth features may comprise, for example, tooth centers, tooth silhouettes, tooth landmarks (e.g., pits, fissures, and/or peaks) or any other tooth features that provide a position and orientation of the subject's teeth. In some examples, the 2D image engine(s) 160 may be further configured to determine virtual camera parameters of the wide angle camera assembly 155 corresponding to the input 2D image. Alternatively, in some examples, a separate analysis engine (e.g., processor) may be included for determining the virtual camera parameters (e.g., a virtual camera parameter engine). The virtual camera parameters can comprise, for example, intrinsic and/or extrinsic camera parameters of the camera assembly corresponding to the input 2D image.

The 3D model engine(s) 162 may implement one or more automated agents to receive and process scan data or 3D dental model data from the scanning system 154. In some examples, the treatment monitoring system 158 is configured to receive, store, and process a 3D model of the subject's dentition 154. The 3D model can comprise, for example a 3D tooth point cloud or a 3D dental mesh model, or a series of 3D tooth point clouds or 3D dental mesh models, each corresponding to a treatment stage; alternatively, the 3D model may include a segmented 3D tooth point cloud or 3D dental mesh model of the teeth and guidance describing the arrangement or configuration of the segmented teeth (and in some examples, gingiva, arch, etc.) and key positions at each stage. The treatment monitoring system 158 is typically configured to generate a rendered 2D image from the 3D dental model using the virtual camera parameters of the camera assembly. The rendered 2D image therefore represents the expected or desired position of the subject's teeth at a particular stage or time in the orthodontic treatment; this stage or time may correspond to the actual time or stage of the input 2D image. The 3D model engine(s) 162 may be further configured to process the rendered 2D image to extract and identify tooth features of the subject's teeth. The tooth features may comprise, for example, tooth centers, tooth silhouettes, or any other tooth features that provide a position and orientation of the subject's teeth, as mentioned above, for comparison with tooth features from the input 2D image.

The tooth comparison engine(s) 164 may implement one or more automated agents to compare the rendered 2D image from the 3D model to the input 2D image from the wide angle camera assembly. The comparison can provide an indication on whether the current position of the subject's teeth tracks with the expected or desired position according to the orthodontic treatment plan. In some examples, the tooth comparison engine provides a difference score (also referred to herein as a comparison value) that may indicate how closely the current position of the subject's teeth is to the desired position; alternatively this score may indicate how different the current position is from the model at a particular treatment stage. The tooth comparison engine may generate one or more difference indicator(s), or comparison indicator(s). A difference indicator may be one or more of: a difference map, a difference score and/or a set of difference values. For example, the difference map may include a 2D or 3D representation of the subject's teeth showing, highlighting or otherwise indicating the difference between the current actual tooth configuration and the desired or predicted tooth configuration from the treatment plan. A difference map may be a colored or marked-up 2D image or images showing differences in position and/or rotation, or a 3D model showing difference in position and/or rotation. The 2D images or 3D models may be annotated with the differences, including the magnitude of the differences. Markings may include heat-map representation of the differences. In some examples, the set of difference values may be a text representation of the differences (and/or similarities) between the current tooth configuration and the treatment plan. The text representation may be a database (e.g., table, listing, or any other data structure).

In some examples, the tooth comparison engine(s) 164 determines and calculates new tooth movements that may be applied to the subject's teeth to achieve the desired position. The tooth comparison engine(s) 164 may also output the difference indicator to the subject (e.g., via a message, alert, etc.) and/or the subject's dental care provider and/or a third party. In some examples, the tooth comparison engine(s) 164 is configured to trigger one or more alerts when the magnitude of the differences between the actual configuration and the treatment plan exceed a threshold value.

The optional treatment modeling engine(s) 166 may be configured to use the new tooth movements to store and/or provide instructions to implement orthodontic treatment plans and/or the results of orthodontic treatment plans. The optional treatment modeling engine(s) (e.g., machine learning engine) 166 may provide the results of orthodontic treatment plans on an updated 3D dental model. In some examples, the updated 3D dental model can include the new tooth movements. The optional treatment modeling engine(s) 166 may model the results of application of orthodontic aligners to the individual's dental arch over the course of an orthodontic treatment plan.

As used herein, any "engine" may include one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some examples, the cloud-based engines can execute functionalities and/or modules that end users access through a web browser or container application without having the functionalities and/or modules installed locally on the end-users' computing devices.

As used herein, "datastores" may include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud based datastore is a datastore that is compatible with cloud-based computing systems and engines.

Figure 1B:
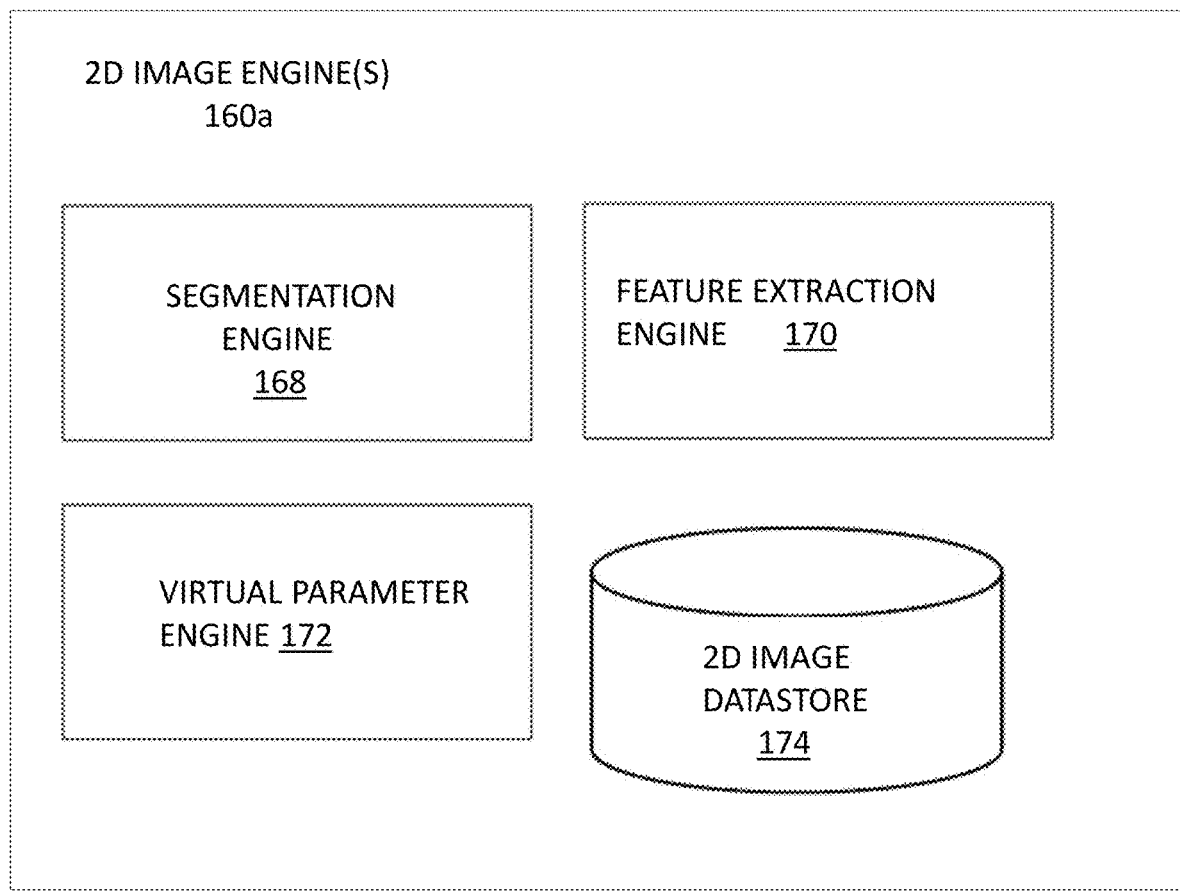
FIG. 1B is a diagram showing an example of 2D image engine(s).

FIG. 1B is a diagram showing a schematic example of a 2D image engine(s) 160a. The 2D image engine(s) 160a may include a segmentation engine 168, a feature extraction engine 170, a virtual parameter engine 172, and a 2D image datastore 174. One or more of the modules of the 2D image engine(s) 162a may be coupled to each other or to modules not shown. The 2D image engine(s) 160a is configured to receive and process an input 2D image of the subject's teeth from a wide angle camera assembly.

Figure 2A:
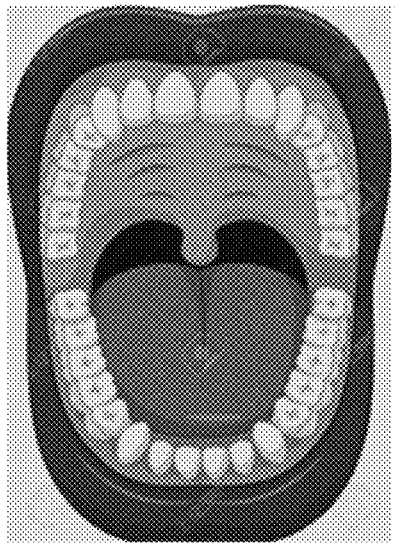
FIGS. 2A-2D show examples of an input 2D image (FIG. 2A) that is segmented (FIG. 2B) and has had tooth features extracted (FIGS. 2C-2D).
Figure 2B:
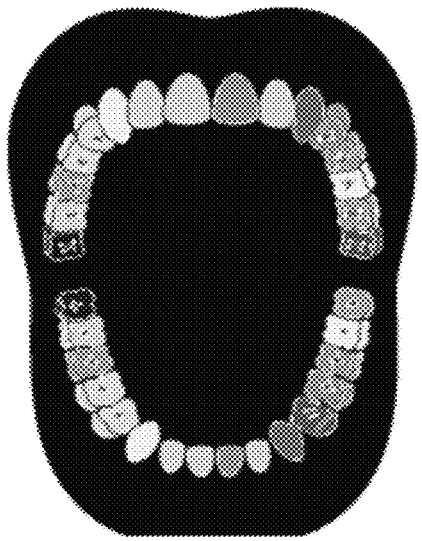

The segmentation engine(s) 168 may implement one or more automated agents configured to process the input 2D image from the wide angle camera assembly 155. The segmentation engine(s) 168 may include graphics engines to process the input 2D image. The segmentation engine(s) 168 may be configured to segment the input 2D image into individual dental components, including segmenting the input 2D image into individual teeth. FIG. 2A is an example of an input 2D image from a wide angle camera assembly. As shown in FIG. 2A, the input 2D image is a single image that includes an occlusal view of both dental arches of the subject's dentition. The wide angle nature of the camera assembly 155 enables this view of both dental arches in a single 2D image. FIG. 2B is an example of the input 2D image after segmentation (e.g., by the segmentation engine). As shown, the input 2D image has been segmented into individual dental components (e.g., teeth) with lower valued image data removed from the image (e.g., gums, lips, palate, etc.). The 2D image datastore 174 may store and provide the input 2D image, the segmented 2D image, and/or other data to other modules of the treatment monitoring system 158.

The methods and apparatuses described herein may benefit from the use of a wide angle camera assembly and the corresponding wide angle input 2D image. These images may be processed as described herein and may be taken without the need for retraction of the cheeks. Thus a subject may take the image themselves (or may have a family member, friend or caregiver take them) quickly and easily. Although these methods and apparatuses may be used with a single wide angle image, in some examples, more than one wide angle image may take and used; in some examples, these images may be combined.

In some examples, the systems and methods described herein may include guidance (e.g., the treatment monitoring system may include an image acquisition guidance engine) for acquiring the input 2D image(s). For example, the system may provide instructions (on the subject's hand-held device) for taking the image, including text, audio, images, video, etc., for positioning and taking the input 2D image. The system may check the quality of the input 2D image taken to ensure that it is in focus, is positioned appropriately (e.g., to give an occlusal view), and/or includes sufficient features (e.g., includes all of the teeth).

Figure 2C:
Figure 2D:
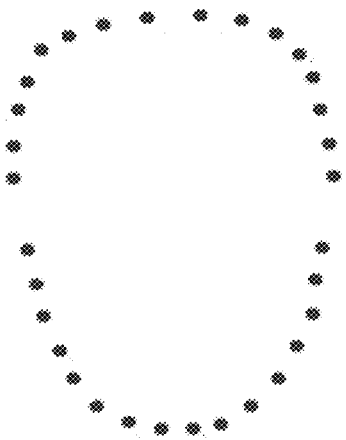

The feature extraction engine(s) 170 may implement one or more automated agents configured to extract dental features from the input 2D image or the segmented input 2D image. A "dental feature," as used herein, may include data points from input 2D image(s) that correlate to centers, silhouettes, edges, contours, vertices, vectors, or surfaces of the subject's teeth. "Dental features" that provide information or details on the orientation of the subject's teeth are particularly useful. For example, dental features may include tooth centers that provide data on the position of the subject's teeth. Similarly, tooth silhouettes may provide data on both the position and orientation of the subject's teeth. FIG. 2C illustrates an example of an input 2D image of a subject's teeth with dental features comprising tooth silhouettes extracted and shown on the 2D image. In contrast, FIG. 2D illustrates only the dental features of tooth centers extracted from the 2D image. While the tooth centers provide data on the position of the individual teeth, the tooth centers may not readily provide sufficient data on the orientation of each tooth. The 2D image datastore 174 may store and provide the extracted features and/or other data to other modules of the treatment monitoring system 158.

The virtual camera parameter engine(s) 172 may implement one or more automated agents configured to determine virtual camera parameters of the wide angle camera assembly corresponding to the input 2D image. The virtual camera parameters of the wide angle camera assembly can comprise extrinsic parameters, which define the location and orientation of the camera assembly with respect to the world frame, and intrinsic parameters, which allow a mapping between camera coordinates and pixel coordinates in the image frame. The virtual parameters of the wide angle (e.g., fisheye) camera assembly can be calculated iteratively, using an optimizer function. In some examples, the 2D image datastore 174 may store and provide virtual camera parameters and/or other data to other modules of the treatment monitoring system 158.

Figure 1C:
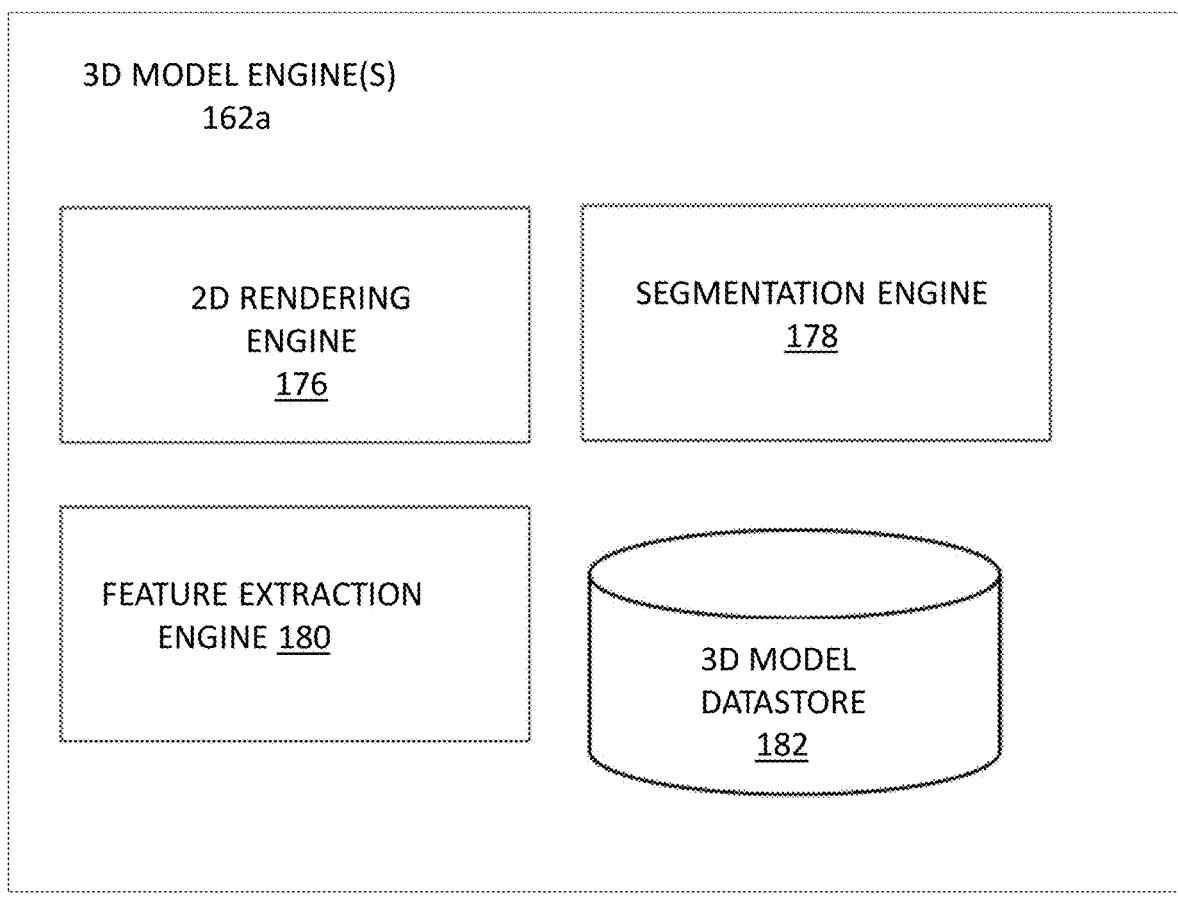
FIG. 1C is a diagram showing an example of 3D model engine(s).

FIG. 1C is a diagram showing an example of the 3D model engine(s) 162a. The 3D model engine(s) 162a may include a 2D rendering engine 176, a segmentation engine 178, a feature extraction engine 180, and a 3D model datastore 182. One or more of the modules of the 3D model engine(s) 162a may be coupled to each other or to modules not shown.

The 2D rendering engine 176 may implement one or more automated agents configured to render a 2D image from the 3D dental model received by the scanning system 154. The 2D image may be rendered from the 3D model using the virtual camera parameters of the wide angle camera assembly from virtual parameter engine 172. The rendered 2D image represents the expected or desired position of the subject's teeth at a particular time or stage in the orthodontic treatment. The 3D model datastore 182 may store and provide the rendered 2D image and/or other data to other modules of the treatment monitoring system 158.

Figure 3A:
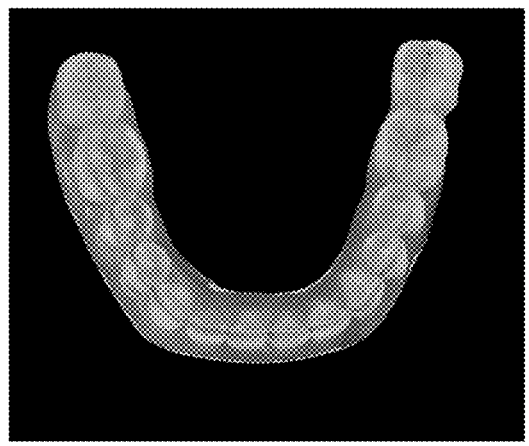
FIG. 3A is an example of a rendered 2D image from a 3D model.

The segmentation engine(s) 178 may implement one or more automated agents configured to process the rendered 2D image from the 2D rendering engine 176. The segmentation engine(s) 178 may include graphics engines to process the rendered 2D image. The segmentation engine(s) 178 may be configured to segment the rendered 2D image into individual dental components, including segmenting the rendered 2D image into individual teeth. As mentioned above, in some examples, the segmentation may be provided or assisted by the 3D model used to generate the rendered 2D image (e.g., the 3D model may be segmented or may include segmentation information). FIG. 3A is an example of a rendered 2D image from the 2D rendering engine. As shown in FIG. 3A, the rendered 2D image is a single image that includes an occlusal view a subject's dental arch. While only a single arch is shown for simplicity, it should be understood that this rendered 2D image can include occlusal views of both dental arches, similar to the input 2D image. The virtual camera parameters may be used to generate this view of the dental arch from the 3D model, as a 2D projection of the 3D model. The 3D model datastore 182 may store and provide the input 2D image, the segmented 2D image, and/or other data to other modules of the treatment monitoring system 158.

The feature extraction engine(s) 180 may implement one or more automated agents configured to extract dental features from the rendered 2D image or the segmented rendered 2D image. A dental feature may include data points from input 2D image(s) that correlate to centers, silhouettes, edges, contours, vertices, vectors, or surfaces of the subject's teeth. Dental features that provide information or details on the orientation of the subject's teeth are particularly useful. For example, tooth centers may provide data on the position of the subject's teeth (translation information). Tooth silhouettes may provide data on both the position and orientation (e.g., rotation) of the subject's teeth. In some examples, as described herein, it may be beneficial (and computational simple) to use tooth centers to determine translational differences between the input 2D images and the treatment plan from the rendered 2D image, while rotational differences may be determined by comparing tooth silhouettes from the input 2D image and the rendered 2D image).

Figure 3B:
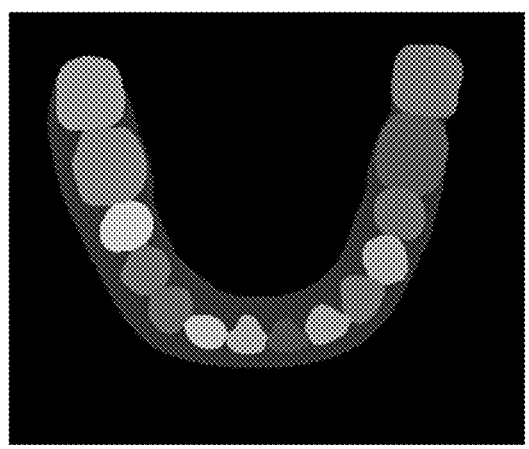
FIG. 3B is an example of a rendered 2D image with tooth features extracted.

FIG. 3B illustrates an example of a rendered 2D image of a subject's teeth with dental features comprising tooth silhouettes extracted and shown on the rendered 2D image. The 3D model datastore 182 may store and provide the extracted features and/or other data to other modules of the treatment monitoring system 158.

FIG. 1D is a diagram showing an example of the tooth comparison engine(s) 164*a*. The tooth comparison engine(s) 164*a* may include a tooth movement engine 184 and a tooth movement datastore 186. One or more of the modules of tooth comparison engine(s) 164*a* may be coupled to each other or to modules not shown.

The tooth movement engine 184 may implement one or more automated agents to compare the rendered 2D image from the 3D model to the input 2D image from the wide angle camera assembly. The comparison of the 2D images can provide an indication on whether the current position of the subject's teeth tracks with the expected or desired position of the subject's teeth according to the orthodontic treatment plan. In some examples, the comparison provides a discrete value (e.g., between 0 and 1) that indicates how closely the subject's teeth are tracking with the orthodontic treatment plan (e.g., a value of 1 would indicate that the subject's teeth are tracking perfectly with the treatment plan, while a value of 0 would indicate that subject's teeth are not tracking at all with the treatment plan). The comparison between the input 2D image and the rendered 2D image can be used to modify the orthodontic treatment plan. For example, the comparison can be used to calculate new teeth movements that are required to move the teeth from the current position to the desired position. The orthodontic treatment plan can be updated with these new teeth movements.

For example, the tooth movement engine may use tooth centers to estimate, for each corresponding tooth in the input 2D image and the rendered 2D image (individual teeth may be identified by the segmentation), differences in the positions of the two types of teeth. For example, the relative translations of the tooth centers may provide an indication of translation differences in tooth positon between the actual and treatment plan positions. Similarly, tooth rotation may be compared between the actual (input 2D image) and the treatment plan (rendered 2D image) by comparison of the tooth silhouettes. The segmentation provides the outline (silhouette) of the tooth as well as an indication of tooth identity (e.g., tooth number). The silhouettes of the teeth of the input 2D image may be compared by rotation of the silhouette to adequately match the silhouette of corresponding teeth from the rendered 2D image and/or the corresponding teeth in the 3D model.

In use, the systems and methods described herein may guide the subject to take a current image (input 2D image) occlusal view of the teeth, compare this current view to the treatment plan at a corresponding (or future) treatment plan stage, and provide an indication of the difference and/or provide guidance to a professional user (e.g., dentist, orthodontist, or other dental professional) in adjusting the treatment plan.

Figure 4A:
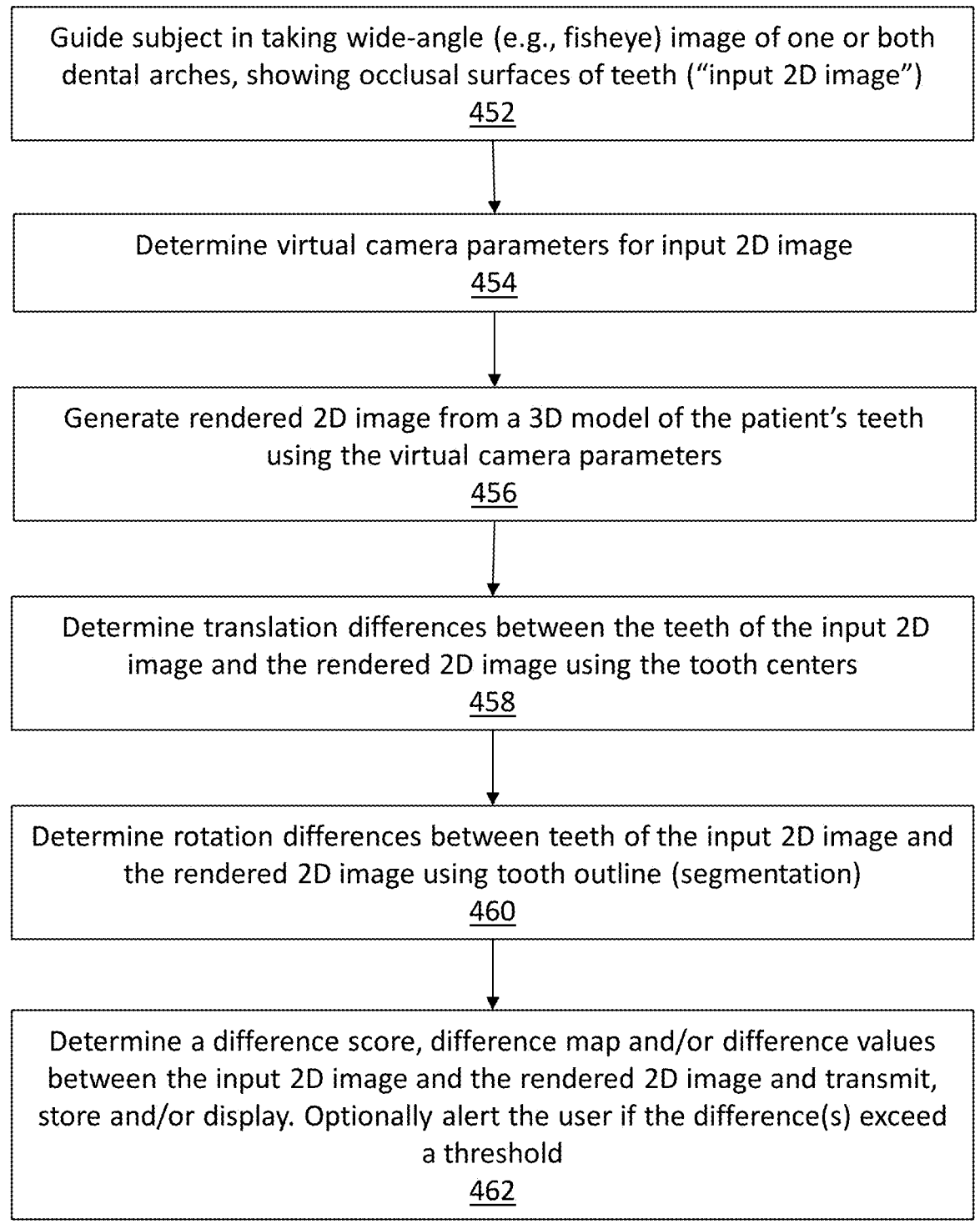
FIG. 4A is one example of a method of monitor a subject's teeth during an orthodontic treatment plan.
Figure 6A:
FIG. 6A is one example of a subject being guided to take a wide angle image (input 2D image) of their upper and lower arches, showing an occlusal view of the teeth.
Figure 7:
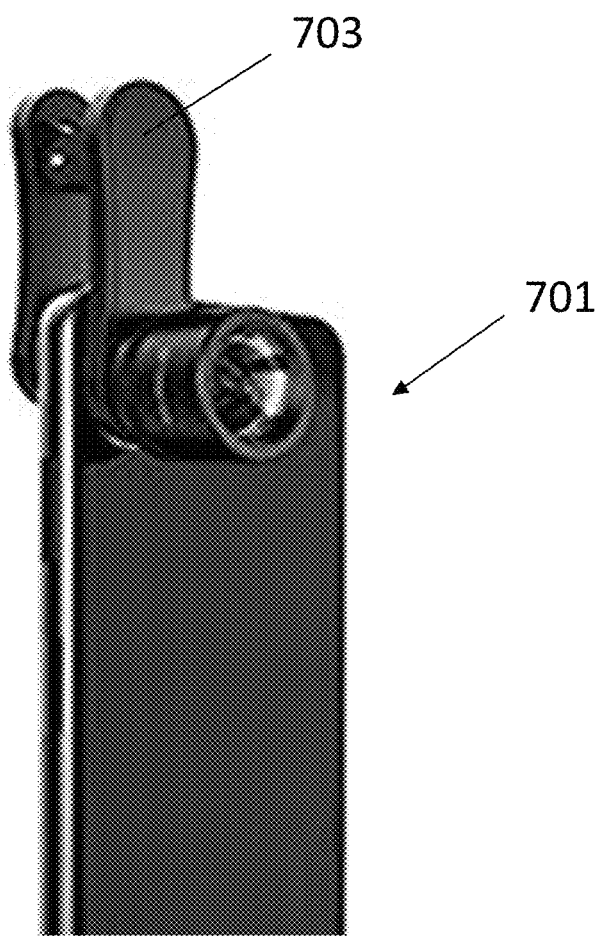
FIG. 7 shows one example of a wide-angle (e.g., fisheye) lens for a smartphone as described herein.

For example, FIG. 4A schematically illustrates one method. In FIG. 4A, the subject (or an agent of the subject, such as a family member, friend, caregiver, etc.) may optionally be guided through the steps of taking a wide angle 2D image of the occlusal view (or perspective occlusal view) of the teeth 452. In some examples, an initial step may include attaching or connecting the wide angle lens or adapter to an existing camera, such a smartphone camera. An example of this is shown in FIG. 6A. FIG. 7 illustrates one example of a wide-angle (e.g., fisheye) lens 703 coupled to a smartphone 701. For example, the subject may be guided to take the image by the system which may provide a visual guide to take the self-photo while looking at the mirror, and/or may provide audio guide to take self-photo without mirror. The system may indicate (e.g., by alert) that the quality of the image taken is not adequate, or may be improved. For example, the system may alert the user subject in case lighting conditions are insufficient. As mentioned, a single image may be used with the wide angle camera assembly, or multiple images may be taken successively with small changes in the angle to assist in achieving better accuracy.

Figure 6B:
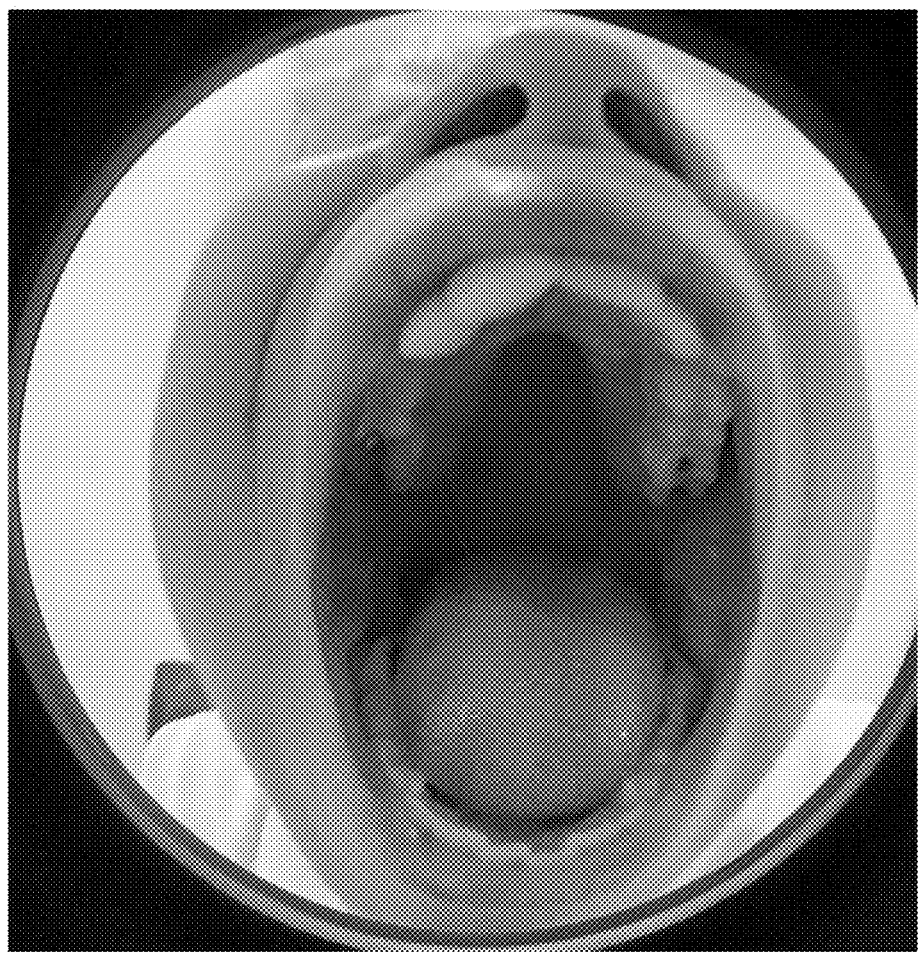
FIG. 6B shows an example of a wide angle occlusal perspective view of the teeth that may be used as 2D input images as described herein.

FIG. 6B illustrates an example of a wide angle image showing an occlusal (occlusal perspective) view of a subject's teeth, taken as described herein. These images may be taken without a retractor, and may be initially analyzed by the apparatus to determine if the image quality is sufficient. In general, the image shown in FIG. 6B is an occlusal perspective view of the upper and lower arch; the wide angle cameral assembly allows concurrent imaging of both upper and lower jaws in the same view. In general, the wide angle 2D images described herein may be referred to as occlusal views because they show primarily (but not exclusively) the occlusal surface of the subject's teeth. These views may also be referred to as occlusal perspective views, as they show a wide angle perspective view of the upper and/or lower jaw occlusal surfaces.

Once the adequate input 2D image is received, the method or system for performing the method may determine the virtual camera parameters for the 2D image 454, as described above. For example, an optimizer may be used to find the camera intrinsic and/or extrinsic parameters by iterating the step of calculating and recalculating the tooth centers corresponding to the adjusting virtual camera parameters. The optimization is such that the projected teeth centers may be projected to image pixels as close as possible to the teeth centers in the image(s). In some examples, the camera assembly may be pre-calibrated, and some or all of the intrinsic parameters may be provided.

A rendered 2D image may then be generated from the 3D model of the patient's teeth (at a corresponding or future treatment stage) using these virtual camera parameters 456. This rendered 2D image may then be compared to the input 2D image, by comparing features between the two images (and/or the 3D model). For example, translational differences between the teeth of the input 2D image and the rendered 2D image may be determined by identifying and comparing the tooth centers of corresponding teeth between the input 2D image and the rendered 2D image 458. Rotational differences between the teeth of the input 2D image and the rendered 2D image may be determined by using the silhouettes of the teeth (e.g., tooth outlines) from the segmented teeth in each image 460. Alternatively, in some examples, the translational differences may also or alternatively be determined from the tooth silhouettes rather than or in addition to the tooth centers.

Based on these comparisons, a difference indicator (e.g., a difference score, difference map and/or difference values) between the input 2D image and the rendered 2D image may be determined, and the difference indicator may be transmitted, stored and/or displayed 462. Optionally, one or more alerts may be transmitted to the subject and/or the subject's dental care provider (e.g., professional user) if the difference(s) exceed a threshold.

Figure 4B:
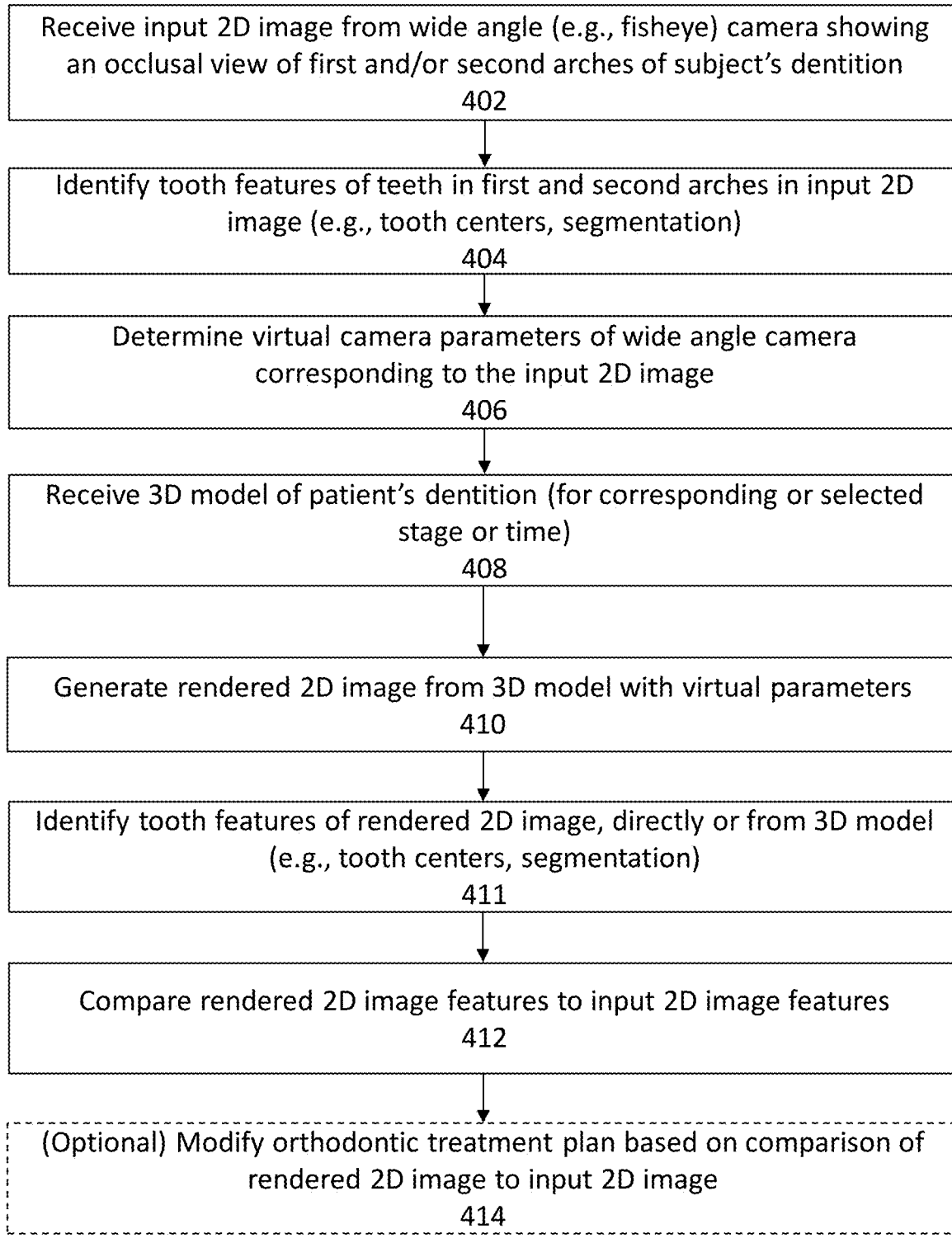
FIG. 4B is another example of a method of monitor a subject's teeth during an orthodontic treatment plan.

FIG. 4B is another example of a flowchart describing a method of monitoring a subject's teeth during an orthodontic treatment plan. As in FIG. 4A, this method may be automatically implemented by a system, such as one or more of the systems in the computing environment 100A, shown in FIG. 1A.

At an operation 402, the method may include receiving an input 2D image from a wide angle camera assembly having an occlusal view of a first arch and a second arch of the subject's dentition. The input 2D image can be taken by the subject using a wide angle camera or a wide angle (e.g., fisheye) lens attachment for a smartphone, tablet, or pc. In some implementations, the input 2D image comprises an occlusal view of both arches of the subject's teeth.

At an operation 404, the method can further include identifying tooth features of teeth in the first arch and second arch in the input 2D image. In some implementations, the tooth features can be identified or extracted with a trained machine learning model. In other implementations, the tooth features can be manually identified or extracted. The tooth features can comprise tooth centers, tooth silhouettes, or other tooth features that provide a position and/or orientation of the subject's teeth.

Next, at an operation 406, the method can further comprise determining virtual parameters of the wide angle camera corresponding to the input 2D image. The virtual parameters of the wide angle camera can comprise extrinsic parameters, which define the location and orientation of the camera with respect to the world frame, and intrinsic parameters, which allow a mapping between camera coordinates and pixel coordinates in the image frame. The virtual parameters of the fisheye lens can be calculated iteratively, such as with an optimizer function.

Next, at an operation 408, the method can include receiving a 3D model of the subject's dentition. The 3D model can be generated and received from a scanning system, such as a 3D dental scanning system. Next, at an operation 410, the method can further include generating a rendered 2D image from the 3D model with the virtual parameters of the wide angle camera (the virtual parameters calculated at operation 406). The rendered 2D image represents an expected or desired positions of the subject's teeth.

At an operation 411, the method can further include identifying tooth features of teeth in the first arch and second arch in the rendered 2D image. In some implementations, the tooth features can be identified or extracted with a trained machine learning model. In other implementations, the tooth features can be manually identified or extracted. The tooth features can comprise tooth centers, tooth silhouettes, or other tooth features that provide a position and/or orientation of the subject's teeth.

Next, at an operation 412, the method can further include comparing the tooth features of the rendered 2D image to the tooth features of the input 2D image. As described above, the comparison of the 2D images can provide an indication on whether the current position of the subject's teeth tracks with the expected or desired position of the subject's teeth according to the orthodontic treatment plan. In some examples, the comparison provides a discrete value between 0 and 1 that indicates how closely the subject's teeth are tracking with the orthodontic treatment plan (e.g., a value of 1 would indicate that the subject's teeth are tracking perfectly with the treatment plan, while a value of 0 would indicate that subject's teeth are not tracking at all with the treatment plan).

Optionally, at an operation 414, the comparison between the input 2D image and the rendered 2D image can be used to modify the orthodontic treatment plan. For example, the comparison can be used to calculate new teeth movements that are required to move the teeth from the current position to the desired position. The orthodontic treatment plan can be updated with these new teeth movements.

In some examples of the methods described herein the comparison between the input 2D image and the reconstructed 2D image may be limited to the tooth centers (e.g., the center of mass of each tooth). The translational differences may provide sufficient rough tracking information for at-home monitoring.

Figure 4C:
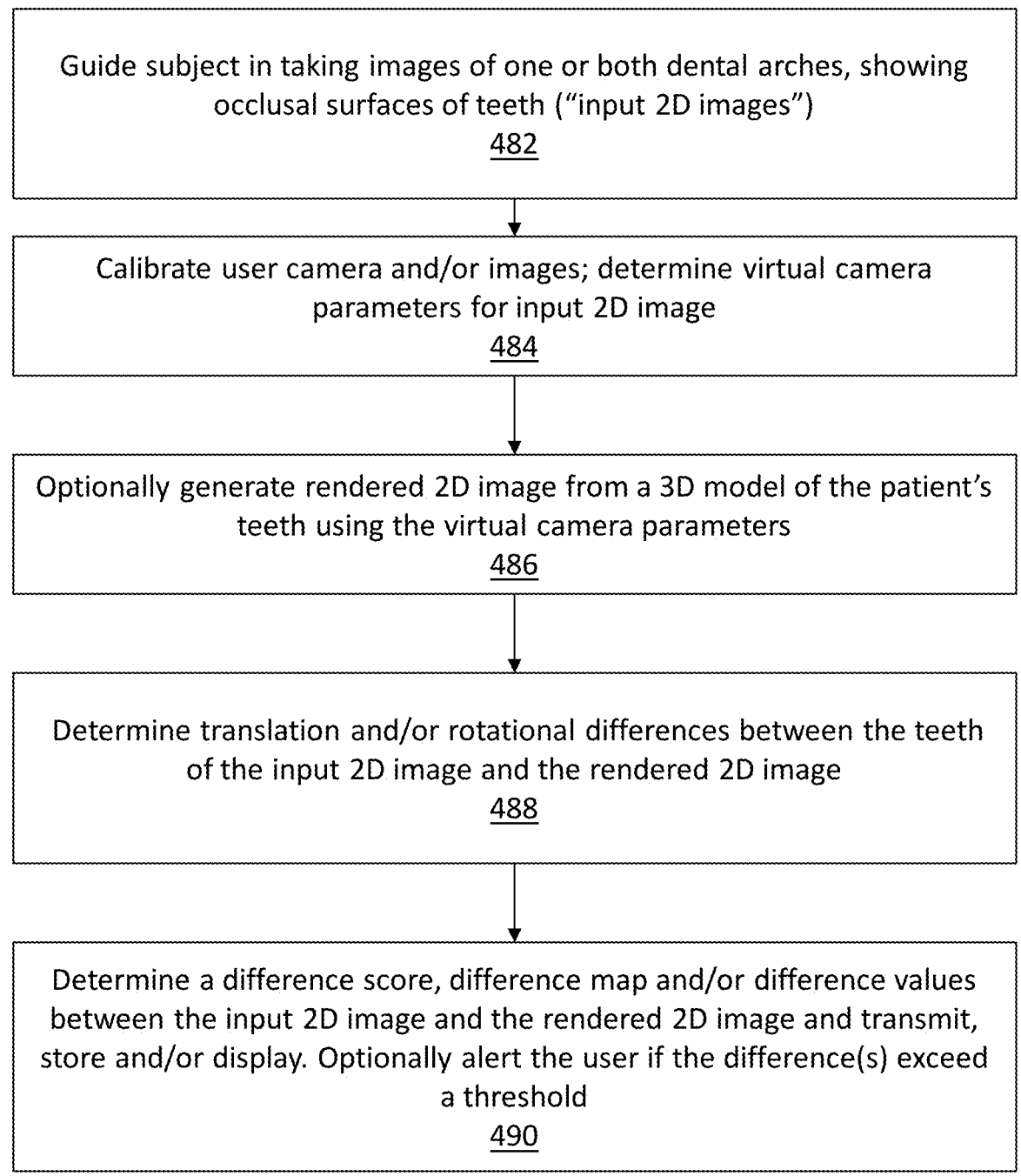
FIG. 4C is another example of a method of monitor a subject's teeth during an orthodontic treatment plan.

In some examples, the methods an apparatuses described herein may be performed without the use of a wide angle lens. For example, these method and apparatuses may be performed using a plurality a camera (e.g., a phone camera) to generate a plurality of images. These images may be combined into a single (pseudo wide-angle) image and processed as described above, or using one or more simplified procedures. For example, FIG. 4C schematically illustrates one such method. In FIG. 4C, the subject (or an agent of the subject, such as a family member, friend, caregiver, etc.) may optionally be guided through the steps of taking a plurality of images of one or both dental arches, including the teeth 482. The camera may be the subject or caregiver's (user subject's) existing camera, such a smartphone camera. For example, the user subject may be guided to take the image by the system which may provide a visual guide to take the self-photo while looking at the mirror, and/or may provide audio guide to take self-photo without mirror. The system may indicate (e.g., by alert) that the quality of the images taken is not adequate, or may be improved. For example, the system may alert the user subject in case lighting conditions are insufficient. Multiple images may be taken successively with small changes in the angle to assist in achieving better accuracy.

Either before or after taking the images, the user subject may calibrate the camera 484. In some examples, the user subject may be instructed to download and/or print an image of a calibration target (e.g., a grid, checkerboard, etc.). The calibration may be performed to determine virtual camera parameters. In some examples, the calibration may help determine the spacing between the camera and the images. The camera intrinsic and/or extrinsic parameters may be identified. In some examples, the multiple images taken may be combined into a singe (merged) image of each (or both) dental arch(s).

One or more rendered 2D image(s) may then be generated from a 3D model of the patient's teeth (at a corresponding or future treatment stage) using these virtual camera parameters 486. This rendered 2D image(s) may then be compared to the input 2D image, by comparing features between the two images (and/or the 3D model). For example, translational and/or rotational differences between the teeth of the input 2D image and the rendered 2D image may be determined.

In some examples, the camera may be registered to the entire jaw, e.g., as part of the calibration. Each tooth may be separately and by that detect the movement of the individual tooth to the entire jaw. This registration may be performed by: matching tooth silhouette projection to the silhouette of the tooth on the image; and/or matching tooth cusps and\or fisher projection to the image tooth cusp and\or fisher projection; and/or using a trained network that takes as an input the tooth image and a depth map of the tooth from the same camera and it produces the teeth movement 488. Alternatively or additionally, rotational differences between the teeth of the input 2D image and the rendered 2D image may be determined by using the silhouettes of the teeth (e.g., tooth outlines) from the segmented teeth in each image. Alternatively, in some examples, the translational differences may also or alternatively be determined from the tooth silhouettes and/or by using the tooth centers.

Based on these comparisons, a difference indicator (e.g., a difference score, difference map and/or difference values) between the input 2D image and the rendered 2D image may be determined, and the difference indicator may be transmitted, stored and/or displayed 490. Optionally, one or more alerts may be transmitted to the subject and/or the subject's dental care provider (e.g., professional user) if the difference(s) exceed a threshold.

Figure 5:
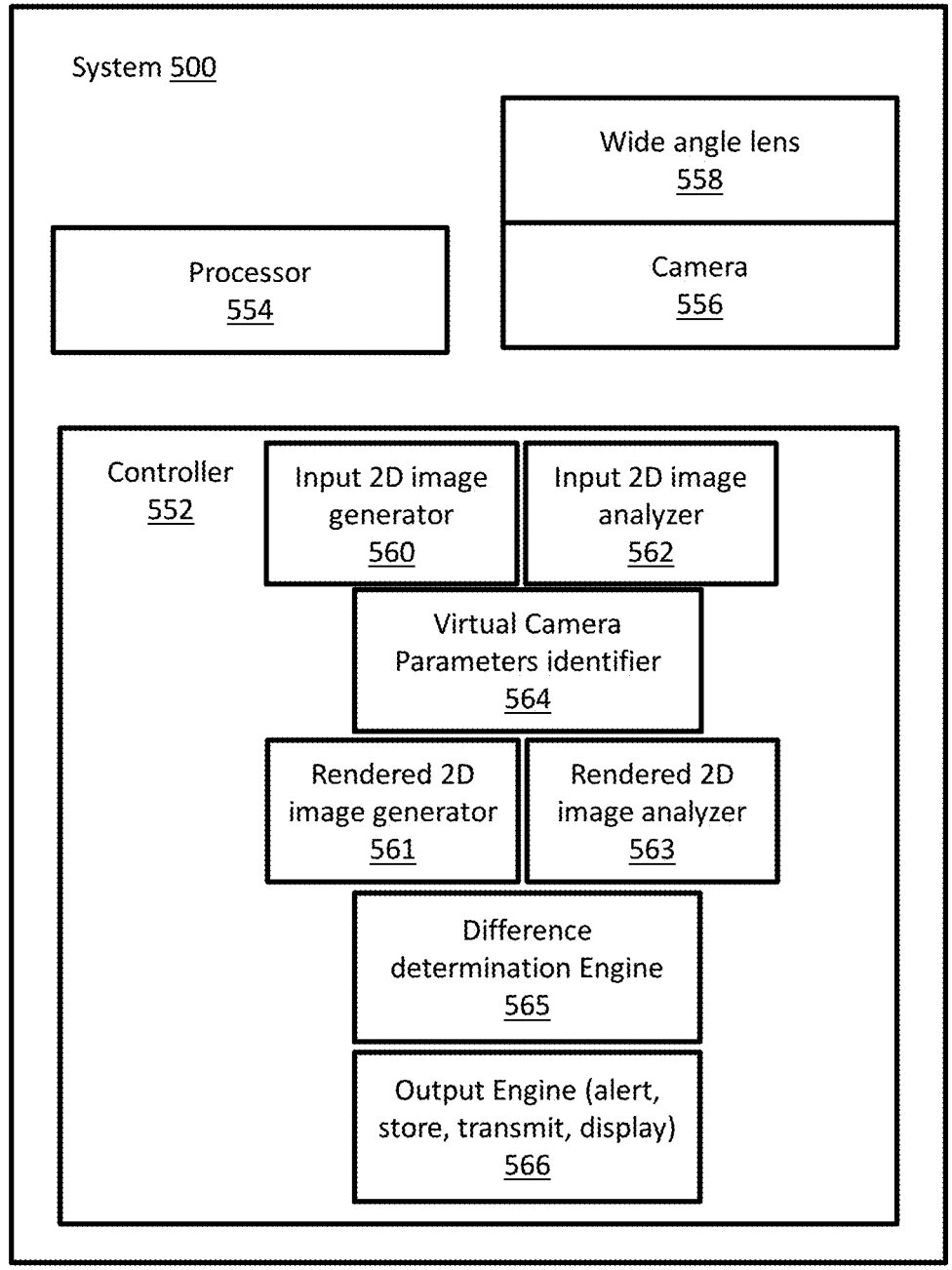
FIG. 5 is an example of a schematic of a system for determining the differences between a subject's actual teeth position and an expected or predicted position of the subject's teeth during a treatment plan.

The methods described herein may be performed by an apparatus, such as a data processing system, which may include hardware, software, and/or firmware for performing many of these steps described above. For example, FIG. 5 is a simplified block diagram of a system 500 as described herein.

Any of these systems 500 may include or be configured to operate on a processor 554, and may include or be configured to operate with a camera assembly including a camera 556 and an integrated or separate wide angle (e.g., fisheye) lens 558. The system may generally include a controller 552 that includes any or all of the modules/engines describe above (e.g., in FIGS. 1A-1D). For example, the controller may include an input 2D image generator 560 and input 2D image analyzer 562 (which may collectively be a 2D input engine). In some examples, the controller may include or operate a virtual camera parameters identifier 564 (which may also be part of the 2D input engine) that may identify the intrinsic and/or extrinsic parameters for the camera assembly. The controller may also include a rendered 2D image generator 561 and a rendered 2D image analyzer 563 (which may be included as part of a 3D model engine). A difference determination engine 565 (e.g., tooth comparison engine) may also be included. Finally, the controller may also include and/or control an output engine 566 that may trigger and present an alert, store, transmit, and/or display the comparison (e.g., difference) indicator(s).

In general, any of these processing systems may include at least one processor which communicates with a number of peripheral devices (which may include all or some of the components described above) over bus subsystem. These peripheral devices may typically include a storage subsystem (e.g., memory subsystem and file storage subsystem), a set of user interface input and output devices, and an interface to outside networks, including the public switched telephone network. This interface may be a modems and network interface, and may be coupled to corresponding interface devices in other data processing systems over communication network interface. These system may include a terminal or a low-end personal computer or a high-end personal computer, workstation or mainframe.

These systems may include a user interface input devices that may include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. A display device may be a cathode ray tube (CRT), a flat-panel device such as a liquid crystal display (LCD), or a projection device. The display subsystem may also provide nonvisual display such as audio output.

A storage subsystem may maintain the basic programming and data constructs that provide the functionality of the present invention. The software modules discussed above may be stored in a storage subsystem. Storage subsystem may comprise a memory subsystem and a file storage subsystem. Memory subsystems may include a number of memories including a main random access memory (RAM) for storage of instructions and data during program execution and a read only memory (ROM) in which fixed instructions may be stored.

File storage subsystems may provide persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. One or more of the drives may be located at a remote location, such as in a server on a local area network or at a site on the Internet's World Wide Web.

A bus subsystem may generically include any mechanism for letting the various components and subsystems communicate with each other as intended. The other components need not be at the same physical location. Thus, for example, portions of the file storage system may be connected over various local-area or wide-area network media, including telephone lines. Similarly, the input devices and display need not be at the same location as the processor, although it is anticipated that the present invention will most often be implemented in the context of PCS and workstations. Bus subsystem may be a single bus or may have a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Various alternatives, modifications, and equivalents may be used in lieu of the above components. Although the final position of the teeth may be determined using computer-aided techniques, a professional user may move the teeth into their final positions by independently manipulating one or more teeth while satisfying the constraints of the prescription.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high level procedural or object-oriented programming language to operate in conjunction with a computer system. However, the programs can be implemented in assembly or machine language, if desired. In any case, the language may be a compiled or interpreted language.

Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

Thus, any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

As mentioned above, any of the apparatuses and methods may include calibration using a calibration standard For example, the patient or caregiver (e.g., user subject) may use a printed calibration standard (e.g., a calibration standard pattern or target, such as a checkerboard pattern) to calibrate the user subject's camera (e.g., a phone camera, a stand-alone camera, a tablet camera, etc.). In some examples the user subject may be provided with a printed calibration standard and/or may be instructed to print out (using a home printer) the calibration standard. The calibration standard may be included with the packaging. In some examples the packaging for the camera or a camera attachment (e.g., adapter, etc.) holding all or some of the optics (such as the wide angle lens) may be configured as a calibration jig that may both position the camera (optionally with the adapter) in a predefined position relative to a calibration standard.

Figure 8A:
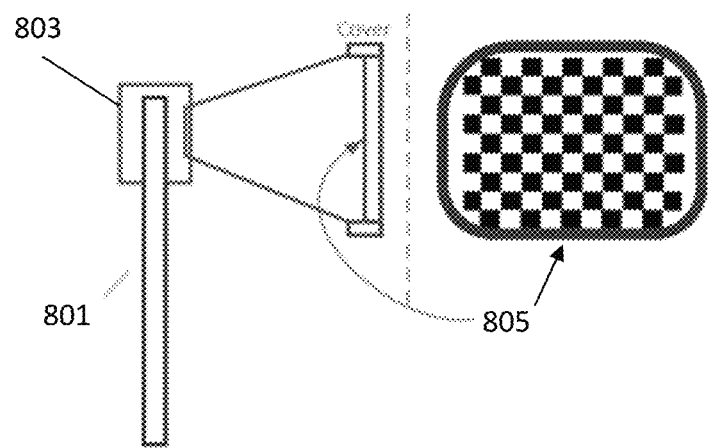
FIG. 8A shows one example of calibration as described herein.
Figure 8B:
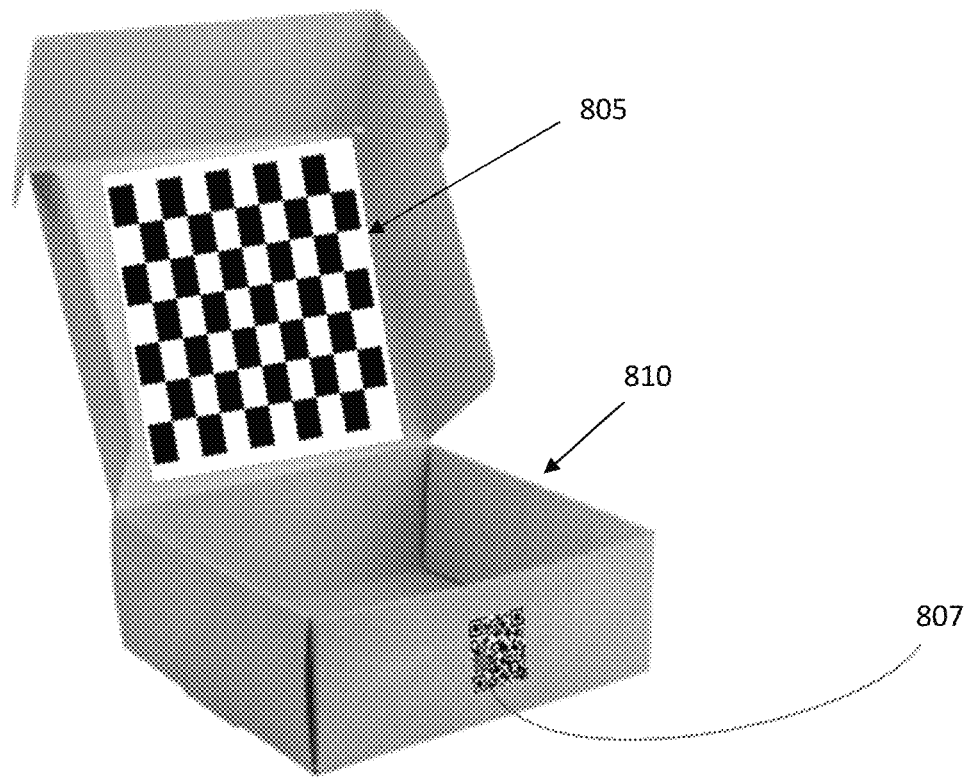
FIG. 8B illustrates one example of calibration using a calibration target on packaging that may be included with the product.
Figure 8C:
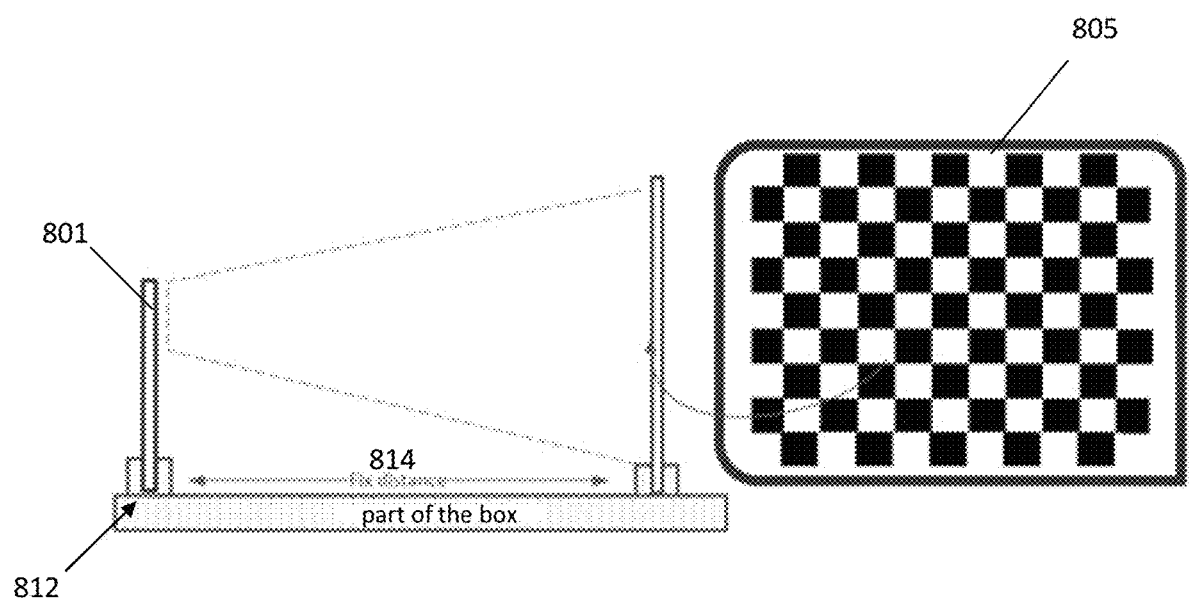
FIG. 8C illustrates one example of a packaging that is also configured as a calibration jig.
Figure 8D:
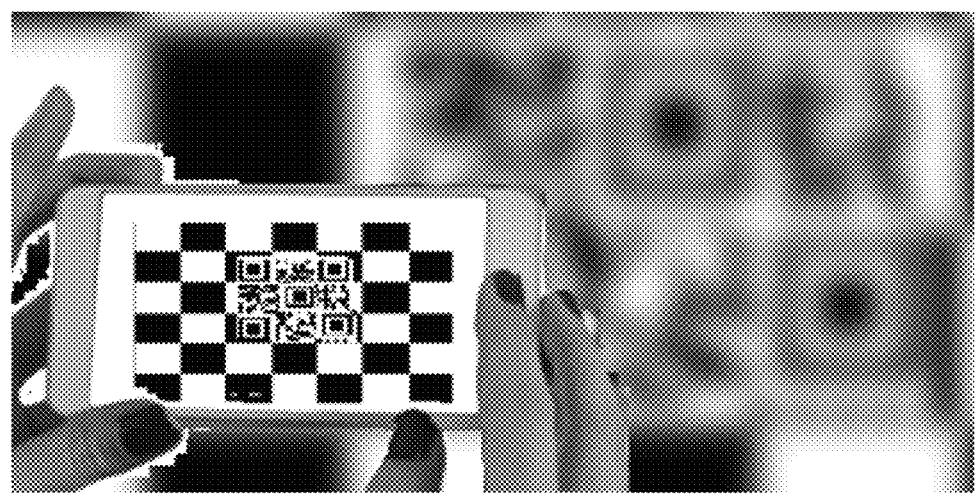
FIG. 8D illustrates one example of a calibration target including a code or link (e.g., QR code).

For example, FIG. 8A schematically illustrates one example of the use of a calibration standard with a user subject's phone. In FIG. 8A, the phone 801 includes an attachment 803 onto the phone to interface with the internal phone camera. The attachment may include one or more lenses (e.g., a wide angle lens). The camera may be calibrated by taking a picture of the calibration target 805, shown in this example a checkerboard pattern. In some examples the checkerboard pattern may be part of a box or packaging 810 that may be provided with the apparatus (e.g., with the attachment that may couple to the user subject's camera. In FIGS. 8A and 8B the calibration pattern is shown printed or attached to the packaging cover. The packaging may also include a code or link 807, e.g., quick response ("QR") code, web address, etc., that may provide link to instructions or application software that may be downloaded to the user subject's camera device (e.g., phone, tablet, etc.) The camera may be linked or registered to the user subject (e.g., patient). The product (apparatus) may be registered, and the application software may assist in taking and/or storing and/or processing the images captured by the user subject's phone. The code or link (e.g., QR code, bar code, alphanumeric code, etc.) may be the calibration target or may be part of the calibration target, as shown in FIG. 8D.

In some examples a calibration frame or jig may be used to hold the user subject's phone at a fixed, predefined distance from the calibration target. For example, the packaging (e.g., box) 810 for the apparatus may include the calibration target and a position location to which the phone may be placed, held, or secured. FIG. 8C illustrates an example of a box that is configured to include a calibration target 805 (e.g., calibration pattern) that is printed on the box, and a stand or holder 812 on the box. In some examples the box includes a hole or opening on a side that the camera may be held against to image a calibration pattern printed or attached within the box. Thus, the camera may image the calibration target at a fixed distance 814 that is predetermined (known), and may therefore calibrate the optical properties (focus, etc.) as a function of the distance. In some examples, multiple calibration targets (at the same or different distances) may be included. For example the packaging may include multiple calibration targets. In some cases the multiple targets may be visible from the same position in which the camera is placed (or held). The target may be compact (as shown in the example of FIG. 8A), or it may be larger (as shown in FIG. 8C).

While preferred embodiments of the present disclosure have been shown and described herein, it will be obvious to those skilled in the art that such embodiments are provided by way of example only. Numerous examples, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one example, the features and elements so described or shown can apply to other examples. It will also be appreciated by those of skill in the art that references to a structure or feature that is disposed "adjacent" another feature may have portions that overlap or underlie the adjacent feature.

Terminology used herein is for the purpose of describing particular examples only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and examples such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and/or methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative examples are described above, any of a number of changes may be made to various examples without departing from the scope of the invention as described by the claims. For example, the order in which various described method steps are performed may often be changed in alternative examples, and in other alternative examples one or more method steps may be skipped altogether. Optional features of various device and system examples may be included in some examples and not in others. Therefore, the foregoing description is provided primarily for exemplary purposes and should not be interpreted to limit the scope of the invention as it is set forth in the claims.

The examples and illustrations included herein show, by way of illustration and not of limitation, specific examples in which the individual matter may be practiced. As mentioned, other examples may be utilized and derived there from, such that structural and logical substitutions and changes may be made without departing from the scope of this disclosure. Such examples of the inventive subject matter may be referred to herein individually or collectively by the term "invention" merely for convenience and without intending to voluntarily limit the scope of this application to any single invention or inventive concept, if more than one is, in fact, disclosed. Thus, although specific examples have been illustrated and described herein, any arrangement calculated to achieve the same purpose may be substituted for the specific examples shown. This disclosure is intended to cover any and all adaptations or examples of various examples. Combinations of the above examples, and other examples not specifically described herein, will be apparent to those of skill in the art upon reviewing the above description.

What is claimed is:

1. A method, the method comprising:
receiving an input two-dimensional (2D) image of a subject's current teeth comprising a wide angle occlusal view of the subject's upper and/or lower jaw at a current treatment stage;
determining virtual camera parameters corresponding to the input 2D image;
receiving a three-dimensional (3D) model of the subject's upper and/or lower jaw at a planned treatment stage;
generating a rendered 2D image of the subject's teeth from the 3D model with the virtual camera parameters;
determining differences between the subject's teeth from the input 2D image and the rendered 2D image using tooth centers; and
outputting a difference indicator indicating the differences between the subject's current teeth and the planned treatment stage based on the difference between the subject's teeth from the input 2D image and the rendered 2D image.

2. The method of claim 1, wherein determining the differences between the subject's teeth from the input 2D image and the rendered 2D image comprises registering individual teeth of the subject's upper and/or lower jaw.

3. The method of claim 2, wherein registering the individual teeth comprises matching tooth silhouette projection between the rendered and input 2D images.

4. The method of claim 2, wherein registering the individual teeth comprises matching tooth cusps and/or fisher projections between the rendered and input 2D images.

5. The method of claim 2, wherein registering the individual teeth comprises using a machine learning agent to determine the differences between the subject's teeth from the input 2D image and the rendered 2D image.

6. The method of claim 1, wherein receiving the input 2D image comprises guiding the subject to take the wide angle occlusal view.

7. The method of claim 1, wherein determining the virtual camera parameters comprises iteratively determining the virtual camera parameters from the input 2D image.

8. The method of claim 1, wherein receiving the input 2D image of the subject's teeth comprises receiving a fisheye view of both the subject's upper and lower jaw.

9. The method of claim 1, further comprising determining a difference score based on the difference indicator and alerting the subject's dental care provider if the difference score exceeds a threshold.

10. The method of claim 1, further comprising updating an orthodontic treatment plan based on the difference indicator.

11. The method of claim 1, further comprising calculating new teeth movements that are required to move the subject's teeth from a current position to a desired position using the difference indicator.

12. The method of claim 11, further comprising updating an orthodontic treatment plan with the new teeth movements.

13. A method, the method comprising:
receiving an input two-dimensional (2D) image of a subject's current teeth comprising a wide angle occlusal view of the subject's upper and/or lower jaw at a current treatment stage;
determining virtual camera parameters corresponding to the input 2D image;
receiving a three-dimensional (3D) model of the subject's upper and/or lower jaw at a planned treatment stage;
generating a rendered 2D image of the subject's teeth from the 3D model with the virtual camera parameters;
determining translation differences between the subject's teeth from the input 2D image and the rendered 2D image using tooth centers;
determining rotational differences between the subject's teeth from the input 2D image and the rendered 2D image using silhouettes of the subject's teeth; and
outputting a difference indicator indicating the differences between the subject's current teeth and the planned treatment stage.

14. A system, the system comprising:
one or more processors;
a camera;
a wide angle lens; and
memory coupled to the one or more processors, the memory configured to store computer-program instructions, that, when executed by the one or more processors, perform a computer-implemented method comprising:
receiving an input two-dimensional (2D) image of a subject's currrent teeth comprising a wide angle occlusal view of the subject's upper and/or lower jaw at a current treatment stage;
determining virtual camera parameters corresponding to the input 2D image;
receiving a three-dimensional (3D) model of the subject's upper and/or lower jaw at a planned treatment stage;
generating a rendered 2D image of the subject's teeth from the 3D model with the virtual camera parameters;
determining differences between the subject's teeth from the input 2D image and the rendered 2D image using tooth centers; and
outputting a difference indicator indicating the differences between the subject's current teeth and the planned treatment stage based on the difference between the subject's teeth from the input 2D image and the rendered 2D image.

15. The system of claim 14, wherein the computer-implemented method further comprises: determining rotational differences between the subject's teeth from the input 2D image and the rendered 2D image using silhouettes of the subject's teeth, wherein the difference indicator is further based on the rotational differences.

16. The system of claim 15, wherein the computer-implemented method further comprises: applying a trained machine learning model to the input 2D image and the rendered 2D image to determine the differences between the subject's teeth from the input 2D image and the rendered 2D image using the tooth centers.

17. The system of claim 15, wherein determining the virtual camera parameters comprises determining extrinsic camera parameters.

18. The system of claim 15, wherein determining the virtual camera parameters comprises iteratively determining the virtual camera parameters from the input 2D image.

19. The system of claim 15, wherein the computer-implemented method further comprises determining a difference score based on the difference indicator and alerting the subject's dental care provider if the difference score exceeds a threshold.

20. The system of claim 15, wherein the computer-implemented method further comprises updating an orthodontic treatment plan based on the difference indicator.

* * * * *